(12) United States Patent
Cranford et al.

(10) Patent No.: US 8,192,628 B2
(45) Date of Patent: *Jun. 5, 2012

(54) PROCESS FOR THE RECOVERY OF OLEAGINOUS COMPOUNDS FROM BIOMASS

(75) Inventors: Richard J. Cranford, San Diego, CA (US); Alex M. Aravanis, San Diego, CA (US); Stilianos G. Roussis, La Jolla, CA (US)

(73) Assignee: Sapphire Energy, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/191,373

(22) Filed: Jul. 26, 2011

(65) Prior Publication Data

US 2012/0022278 A1 Jan. 26, 2012

Related U.S. Application Data

(60) Provisional application No. 61/432,006, filed on Jan. 12, 2011, provisional application No. 61/367,763, filed on Jul. 26, 2010.

(51) Int. Cl.
*B01D 11/00* (2006.01)

(52) U.S. Cl. ............ 210/639; 44/307; 44/605; 210/749; 210/770; 210/774; 210/787; 210/804; 210/806

(58) Field of Classification Search .................. 44/307, 44/308, 605; 47/1.4; 554/12–16, 20, 21; 210/634, 639, 743, 749, 770, 774, 806, 632, 210/787, 800, 804; 435/134, 262, 267, 271, 435/272

See application file for complete search history.

(56) References Cited

U.S. PATENT DOCUMENTS

| 2,635,104 A | 4/1953 | Chayen |
| 3,983,008 A | 9/1976 | Shinozaki et al. |
| 4,418,191 A | 11/1983 | Irvin |
| 4,670,613 A | 6/1987 | Ruyter et al. |
| 4,992,605 A | 2/1991 | Craig et al. |
| 5,130,242 A | 7/1992 | Barclay |
| 5,472,472 A | 12/1995 | Northrop |
| 5,928,696 A | 7/1999 | Best et al. |
| 5,939,229 A | 8/1999 | Robbins |
| 6,166,230 A | 12/2000 | Bijl et al. |
| 6,166,231 A | 12/2000 | Hoeksema |
| 6,180,376 B1 | 1/2001 | Liddell |
| 6,180,845 B1 | 1/2001 | Catallo et al. |
| 6,399,803 B1 | 6/2002 | Corley et al. |

(Continued)

FOREIGN PATENT DOCUMENTS

EP 0170991 A1 2/1986

(Continued)

OTHER PUBLICATIONS

Andorich et al., "Supercritical fluid extraction for Micalga *Spirulin* (*Arthrospira*) *plantesis*." Acta Alimemtaria, 2006, vol. 35, pp. 195-203.

(Continued)

*Primary Examiner* — Joseph Drodge
(74) *Attorney, Agent, or Firm* — Sapphire Energy, Inc.

(57) ABSTRACT

Disclosed herein are methods and processes for the recovery of oleaginous compounds from biomass and in particular biomass comprises photosynthetic microorganisms. Also disclosure are oleaginous compounds obtained using the disclosed methods.

19 Claims, 2 Drawing Sheets

U.S. PATENT DOCUMENTS

| | | | |
|---|---|---|---|
| 6,692,642 B2 | 2/2004 | Josse et al. | |
| 7,179,379 B2 | 2/2007 | Appel et al. | |
| 7,232,935 B2 | 6/2007 | Jakkula et al. | |
| 7,262,331 B2 | 8/2007 | van de Beld et al. | |
| 7,297,261 B2 | 11/2007 | Bomberger et al. | |
| 7,425,412 B2 | 9/2008 | Lo et al. | |
| 7,431,952 B2 | 10/2008 | Biji et al. | |
| 7,476,296 B2 | 1/2009 | Appel et al. | |
| 7,491,858 B2 | 2/2009 | Murzin et al. | |
| 7,692,050 B2 | 4/2010 | Adams et al. | |
| 7,771,699 B2 | 8/2010 | Adams et al. | |
| 7,883,882 B2* | 2/2011 | Franklin et al. | 435/196 |
| 7,935,515 B2* | 5/2011 | Franklin et al. | 435/257.1 |
| 8,003,833 B2 | 8/2011 | Appel et al. | |
| 2004/0011575 A1 | 1/2004 | Shimada et al. | |
| 2004/0074760 A1 | 4/2004 | Portnoff et al. | |
| 2004/0192980 A1 | 9/2004 | Appel et al. | |
| 2008/0044875 A1 | 2/2008 | Ruecker et al. | |
| 2008/0305445 A1 | 12/2008 | Roberts et al. | |
| 2008/0308457 A1 | 12/2008 | Dindi et al. | |
| 2009/0047721 A1 | 2/2009 | Trimbur et al. | |
| 2009/0062581 A1 | 3/2009 | Appel et al. | |
| 2009/0069610 A1 | 3/2009 | Roberts, IV et al. | |
| 2009/0126260 A1 | 5/2009 | Aravanis et al. | |
| 2009/0234146 A1* | 9/2009 | Cooney et al. | 554/174 |
| 2009/0266743 A1 | 10/2009 | Yao et al. | |
| 2009/0298159 A1 | 12/2009 | Wu et al. | |
| 2010/0028962 A1 | 2/2010 | Hu et al. | |
| 2010/0040527 A1 | 2/2010 | Randhava et al. | |
| 2010/0050502 A1 | 3/2010 | Wu et al. | |
| 2010/0147766 A1 | 6/2010 | Nissen et al. | |
| 2010/0239712 A1 | 9/2010 | Brooks et al. | |
| 2010/0297749 A1 | 11/2010 | Aravanis et al. | |
| 2010/0330615 A1* | 12/2010 | Neto | 435/42 |
| 2011/0041386 A1* | 2/2011 | Fleischer et al. | 44/308 |
| 2011/0072713 A1* | 3/2011 | Fleischer et al. | 44/388 |
| 2011/0086386 A1 | 4/2011 | Czartoski et al. | |
| 2011/0092725 A1 | 4/2011 | Jones | |
| 2011/0124034 A1 | 5/2011 | Kuehnle et al. | |
| 2011/0195085 A1* | 8/2011 | Kale | 424/195.17 |
| 2011/0232344 A1* | 9/2011 | Miller et al. | 71/11 |

FOREIGN PATENT DOCUMENTS

| | | |
|---|---|---|
| EP | 1320388 B1 | 11/2005 |
| WO | WO 96/28014 A1 | 9/1996 |
| WO | WO 97/04121 A1 | 2/1997 |
| WO | WO 2007/012643 A1 | 2/2007 |
| WO | WO 2007/027955 A2 | 3/2007 |
| WO | WO 2007/068795 A1 | 6/2007 |
| WO | WO 2007/112570 A1 | 10/2007 |
| WO | WO 2008/029301 A2 | 3/2008 |
| WO | WO 2008/103204 A2 | 8/2008 |
| WO | WO 2009/064204 A2 | 5/2009 |
| WO | WO 2009/085324 A1 | 7/2009 |
| WO | WO 2010/000416 A1 | 1/2010 |
| WO | WO 2010/002886 A1 | 1/2010 |
| WO | WO 2010/030197 A1 | 3/2010 |
| WO | WO 2010/043765 A1 | 4/2010 |
| WO | WO 2010/069516 A2 | 6/2010 |
| WO | WO 2011/025616 A2 | 3/2011 |

OTHER PUBLICATIONS

Aresta et al., "Production of biodiesel from macroalgae by supercritical CO2 extraction and thermochemcial liquefaction." Environ. Chem. Lett., 2005, vol. 3, pp. 136-139.

Brown et al., "Hydrothermal liquefaction and gasification of *Nannochloropsis* sp." Energy and Fuels,. 2010, vol. 24, pp. 3639-3646.

Dote et al., "Recovery of liquid fuel form hydrocarbon-rich micoralgae by thermochemical liquefaction." Fuel, 1994, vol. 73, pp. 1855-1857.

Fu et al., "Catalytic hydrothermal deoxygenation of palmitic acid." Energy Environ. Sci., 2010, vol. 3, pp. 311-317.

Goudriaan et al., "Liquid fuels from biomass via a hydrothermal process." Chem. Eng. Sci., 1990, vol. 45, pp. 2729-2734.

Holliday et al., "Hydrolysis of vegetable oils in sub- and supercritcal water." Ind. Eng. Chem. Res., 1997, vol. 36, pp. 932-935.

Huber et al., "Synthesis of transportation fuels from biomass: chemistry, catalysts, and engineering." Chem. Rev., 2006, vol. 106, pp. 4044-4098.

Jena et al., "Effect of operating conditions of thermochemical liquefaction on biocrude prodution from *Spirulina platensis*." Bioresource Technology, 2011, vol. 102, pp. 6221-6229.

Matsui et al., "Liquefaction of micro-algae with iron catalyst.." Fuel, 1997, vol. 76, pp. 1043-1048.

Minowa et al, "Oil production from algal cells of *Dunaliella tertiolecta* by direct thermochemical liquefaction," Fuel 1995, vol. 74(12); 1735-1738.

Patil et al., "Towards sustainable production of biofuels from microalgae." Int. J. Mol. Sci., 2008, vol. 9, pp. 1188-1195.

Peterson et al., "Thermochemcial biofuel production in hydrothermal media: A review of sub- and supercritical water technologies." Energy & Environmental Science, 2008, vol. 1, pp. 32-65.

Ross et al., "Hydrothermal processing of microalgae using alkali and organic acids." Fuel, 2010, vol. 89, pp. 2234-2243.

Shuping et al., "Production and characterization of bio-oil from hydrothermal liquefaction of microalgae *Dunaliella tertiolecta* cake." Energy, 2010, vol. 35, pp. 5406-5411.

Sonntag, "Fat splitting." J. Am. Oil Chemists' Soc., 1979, vol. 56, pp. 729A-732A.

Valdez et al., "Characterization of product fractions for hydrothermal liquefaction of *Nannochloropsis sp* and the influence of solvents." Energy & Fuels, 2011, vol. 25, pp. 3235-3243.

Yang et al., Analysis of energy conversion characteristics in liquefaction of algae. Resources Conservation and Recycling, 2004, Vo. 43, pp. 21-33.

Yeoman et al., "The removal of phosphorus during wastewater treatment: A review." Environmental Pollution, 1983, vol. 49, pp. 183-233.

Peterson et al., "Kenetic Evidence of the Mallard Reaction in Hydrothermal Biomass Processing: Glucose-Glycine Interactions in High-Temperature, High-Pressure Water." Ind. Eng. Chem. Res., 2010, vol. 49., pp. 2107-2117.

\* cited by examiner

PROCESS FOR THE RECOVERY OF OLEAGINOUS COMPOUNDS FROM BIOMASS

CROSS REFERENCE TO RELATED APPLICATIONS

This application claims the benefit of U.S. Provisional Patent Application Ser. No. 61/367,763, filed Jul. 26, 2010, and U.S. Provisional Patent Application Ser. No. 61/432,006, filed Jan. 12, 2011, each of which is herein incorporated by reference in its entirety for all purposes.

BACKGROUND

Fuel products, such as oil, petrochemicals, and other substances useful for the production of petrochemicals are increasingly in demand. By 2030, energy demand, primarily in the form of oil and gas, is projected to increase by 45%. In many countries, there is a disparity between oil use and oil production. For example, it is estimated that during the year 2008, the United States consumed approximately 19 million barrels of oil per day while producing only about 8 million barrels per day. This disparity is projected to markedly increase in the future as domestic production plateaus or declines. For economic and national security reasons, there is a renewed emphasis on the development of alternative sources of hydrocarbons other than fossil fuels.

In addition, the burning of fossil fuels has been associated with increasing levels of carbon dioxide in the earth's atmosphere. This increase in carbon dioxide has, in turn, been associated with a gradual increase in the earth's temperature. By some estimates, the average global temperature may rise as much as 6° C. by the end of the century if carbon emissions are not reduced. Such a global temperature rise could have a substantial effect on human civilization due to such things as coastal flooding and crop failures. As a result, there has been increased interest in developing energy resources that are carbon neutral or result in greatly reduced net $CO_2$ production. Also, as fossil fuels become technically more difficult to obtain, public awareness regarding pollution and environmental hazards in the production of fossil fuels has increased.

As a result, there has been a growing interest and need for alternative methods to produce fuel products. Biomass, and in particular lipid containing microorganisms, provides an alternative source of hydrocarbons for use as fuels. Photosynthetic microorganisms, such as photosynthetic microalgae and photosynthetic bacteria, are especially useful due to their ability to remove carbon dioxide from the atmosphere and the fact that they do not directly compete with food production for resources.

Algae are highly adaptable plants that are capable of rapid growth under a wide range of conditions. Most algal species are adapted for growth in an aqueous environment and can be grown in liquid media using light as an energy source. The ability to grow algae on a large scale in an outdoor setting, in ponds or other open or closed containers, using sunlight for photosynthesis, enhances their utility for bioproduction of energy, environmental remediation, and carbon fixation.

Critical to the use of aquatic microorganisms for the production of fuels, is the ability to efficiently and economically recover the oil from the organisms. Given that the majority of photosynthetic algae and bacteria are aquatic, it is preferable that the method be suitable for recovering oil from biomass with a high water content.

SUMMARY

Among the many embodiments described herein is a method for obtaining an oleaginous composition from biomass comprising obtaining a feedstock comprising biomass and water, heating the aqueous composition, with or without mixing, in a closed reaction vessel to a temperature between about 220° C. and about 500° C. and holding the aqueous composition at the temperature between 0 minutes (i.e. no hold time) and about 4 hours. The feedstock may or may not have been subjected to pretreatment as described herein. The feedstock is cooled to from ambient temperature to about 150° C. and then acidified to a pH between about 2.0 and 6.0. The acidified composition is heated to between about 40° C. and about 150° C. and held at that temperature, with or without mixing, for a period ranging from 0 minutes (i.e. no hold time) to about 4 hours. The acidified composition can then be allowed to phase separate into at least an organic phase and an aqueous phase without further processing and the organic phase removed. In some instances, at least a third particulate or solids phase may also be present. Alternatively or in addition, solvent extraction can be used. If solvent extraction is used, a volume of solvent approximately equal to the volume of water in the acidified composition is added to produce a solvent extraction composition. The solvent used may be one which is insoluble or substantially insoluble in water but in which oleaginous compounds are soluble or substantially soluble. The solvent extraction composition is brought to a temperature of between about 20° C. and about 150° C. and the composition is held at that temperature, with or without mixing, for a period ranging for 0 minutes (i.e. no hold time) to about 4 hours. The solvent extraction composition is separated into at least an organic layer and an aqueous layer. In some embodiments at least a particulates or solids layer is also present. The organic layer is then obtained and the solvent removed to obtain the oleaginous compound(s) in the organic layer.

In some embodiments, the biomass is subject to a pretreatment which comprises heating the biomass to a temperature between about 80° C. and about 220° C. after which the liquid or aqueous phase may be removed. The biomass is held at this temperature, with or without stirring or agitation for between about 5 minutes and about 60 minutes. In certain embodiments, the material is held between about 170° C. and 210° C. for between about 20 minutes and 40 minutes. In some embodiments, an acid is added to the biomass during the pretreatment, and in particular during heating. In certain embodiments, the of the biomass is adjusted to between about pH 3 and pH 6 during the pretreatment. In additional embodiments, the pretreatment further comprises rinsing the biomass following removal of the liquid phase. In certain embodiments, rinsing comprises addition of water, for example deionized water, equal to the volume of the liquid phase removed, mixing the biomass and water for between about 5 and 30 minutes are ambient temperature, and removing the rinse liquid. In further embodiments, an amount of water, for example deionized water, equal to the amount of liquid removed is added to the biomass after pretreatment and before further processing.

In additional embodiments, pretreated biomass is stored prior to further processing. The pretreated biomass may be stored for any desired time, for example from between 1 day and 1 year. The pretreated biomass may be stored at ambient temperature or at a controlled temperature between about −20° C. and 25° C. The pretreated biomass may be stored in an open or closed container. If stored in a closed container, the atmosphere in the container may be air, or a gas such as nitrogen, carbon dioxide, argon or a combination thereof.

In certain embodiments, the biomass comprises an aquatic microorganism such as an alga or a bacterium. In further embodiments, the aquatic microorganism is photosynthetic, for example, a photosynthetic alga or cyanobacterium.

Another aspect, provides an oleaginous composition made by any of the processes described herein. In certain embodiments the oleaginous composition is obtained from a photosynthetic microorganism and has a calcium content of less than 30 ppm, a magnesium content of less than 20 ppm, a manganese content of less than 20 ppm, a phosphorus content of less than 20 ppm, a sodium content of less than 50 ppm and a strontium content of less than 20 ppm.

Yet another aspect provides for an oleaginous composition obtained from aquatic biomass which has a calcium content of less than 30 ppm, a magnesium content of less than 20 ppm, a manganese content of less than 20 ppm, a phosphorus content of less than 20 ppm, a sodium content of less than 50 ppm and a strontium content of less than 20 ppm. In certain embodiments the aquatic biomass comprises a photosynthetic organism, for example an photosynthetic alga or a cyanobacterium. In further embodiments the alga is a microalga.

A further aspect provides an oleaginous composition comprising an oil extracted from biomass of a microorganism having a percent mass fraction with a boiling point between 260° F. and 630° F. of between about 5% and 55% as determined by ASTM protocol D7169-11. In one embodiment, the oil has a percent mass fraction with a boiling point of from 260° F. and 630° F. of between about 20% and 35% as determined by ASTM protocol D7169-11, in another embodiment, the oil has a percent mass fraction with a boiling point of from 260° F. and 630° F. of between about 30% and 45% as determined by ASTM protocol D7169-11. In certain embodiments, the oil has not be subjected to one or more of hydrotreating, decarboxylation, decarbonylation, hydrodeoxygenation, isomerization (including hydroisomerization), desulfurization, denitrogenation, hydrocracking and catalytic cracking. The microorganism can be a photosynthetic or non-photosynthetic alga or bacterium. In one embodiment, the alga is a photosynthetic microalga, while in another embodiment the microorganism is a cyanobacterium.

Another aspect provides an oleaginous composition comprising an oil extracted from biomass of a microorganism having a percent mass fraction with a boiling point of from 490° F. to 630° F. of between about 25% and about 35% as determined by ASTM protocol D7169-11. In one embodiment, the oil has a percent mass fraction with a boiling point of from 490° F. to 630° F. of between about 20% and about 30%. In certain embodiments, the oil has not be subjected to one or more of hydrotreating, decarboxylation, decarbonylation, hydrodeoxygenation, isomerization (including hydroisomerization), desulfurization, denitrogenation, hydrocracking and catalytic cracking. The microorganism can be a photosynthetic or non-photosynthetic alga or bacterium. In one embodiment, the alga is a photosynthetic microalga, while in another embodiment the microorganism is a cyanobacterium.

BRIEF DESCRIPTION OF THE DRAWINGS

These and other features, aspects, and advantages of the present invention will become better understood with regard to the following description, appended claims and accompanying figures, where:

DETAILED DESCRIPTION

Figure 1:
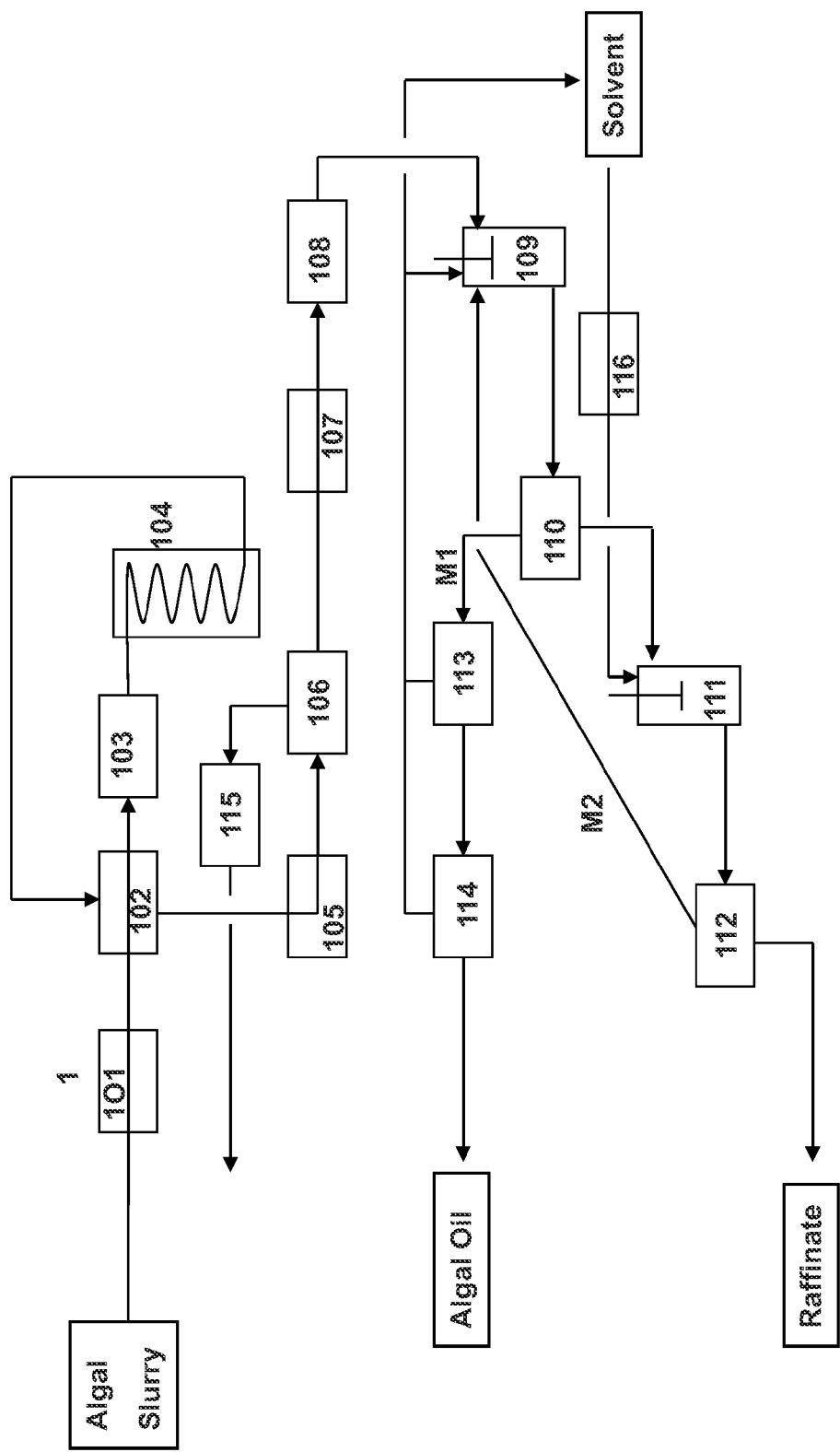
FIG. 1 shows a schematic representation of one embodiment of the disclosed processes in which a continuous countercurrent extraction process is used.
Figure 2:
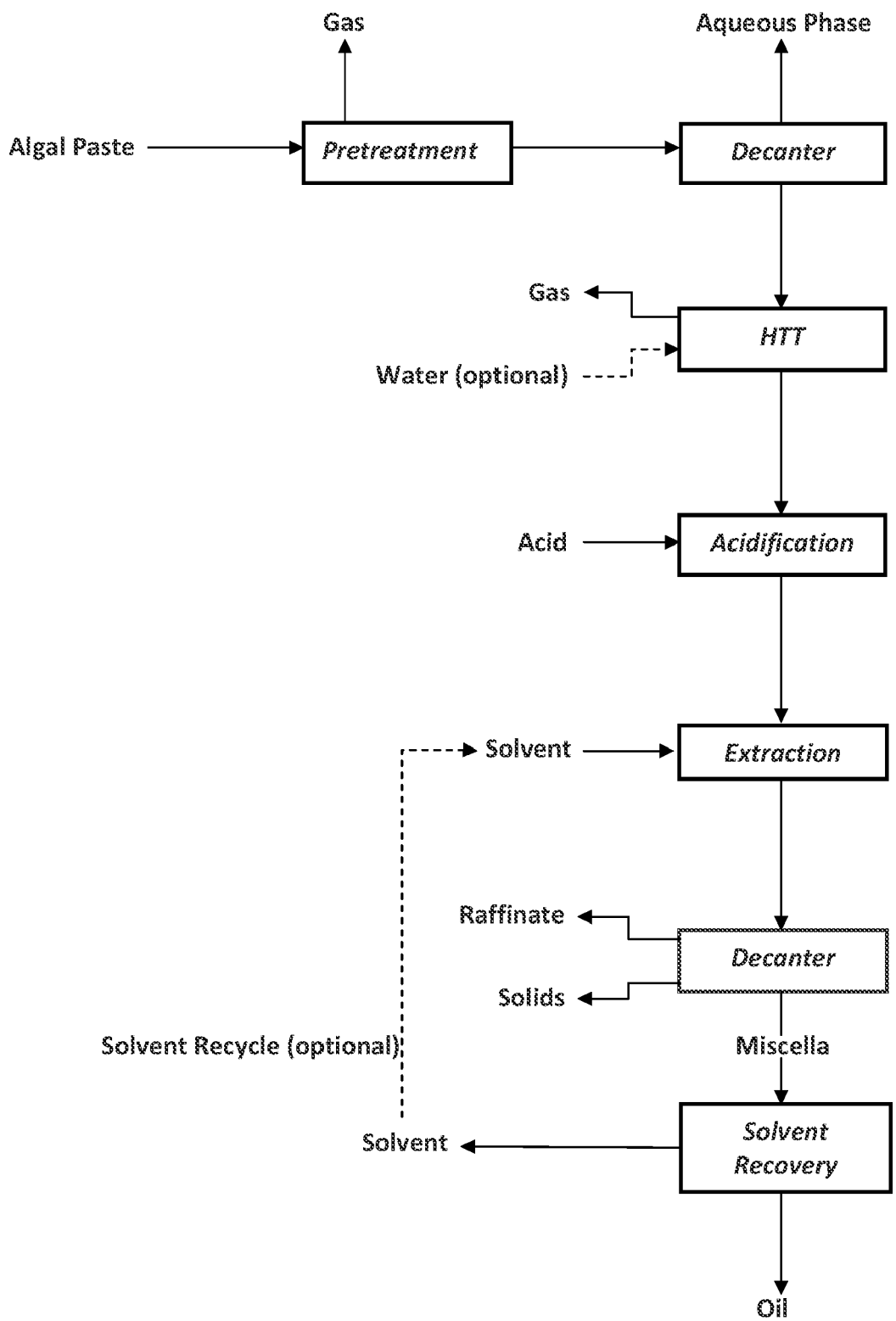
FIG. 2 shows a schematic representation of one embodiment of the disclosed processes in which pretreatment is used.

The following detailed description is provided to aid those skilled in the art in practicing the disclosed embodiments. Even so, this detailed description should not be construed to unduly limit the present invention as modifications and variations in the embodiments discussed herein can be made by those of ordinary skill in the art without departing from the scope of the present inventive discovery.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

As used in this specification and the appended claims, the singular forms "a", "an" and "the" include the plural reference unless the context clearly dictates otherwise.

As used in this specification and appended claims, any range of values described as between two endpoints comprises the endpoints. For example, the range between 220° C. and 500° C. includes 220° C. and 500° C. as well as all values in between.

As used in this specification and appended claims, the terms "hydrothermal treatment" and "hydrothermal process" are used interchangeably.

As used in this specification and appended claims, the term "biomass" refers to a composition of biological origin that is alive or has been alive within the last 50 years.

Provided herein are methods and processes for obtaining an oleaginous compound or compounds from biomass and in particular from a microorganism. By an oleaginous compound is meant a compound having the properties of an oil. Thus, oleaginous compounds include hydrocarbons or lipids. Non-limiting examples of oleaginous compounds include, waxes; fatty acyls including free fatty acids, fatty esters and fatty amides; glycerolipids such as mono, di and tri glycerides; glycerophospholipids; sphingolipids such as phosphosphingolipids and glycosphingolipids; sterols; terpenes such as isoterpenes, isoprenes, terpenoids and isoprenoids; saccharolipids; polyketides; carotenoids, chlorophylls and other pigments. It is to be understood that any compound that can be extracted from biomass and refined into a fuel or lubricant may, in some embodiments, be considered an oleaginous compound.

There currently exists an extensive infrastructure for the transportation, refining, distribution and use of fuels obtained from geologic petroleum (fossil fuels). The ability of any alternative fuel source to utilize this existing infrastructure presents a distinct advantage in terms of rapid adoption and cost competitiveness. Presently, many alternative fuels are not suited for use in the existing petroleum infrastructure. For example, ethanol is incompatible with existing distribution networks due to its tendency to absorb water. In addition, existing gasoline engines require modification before they can burn fuels containing high amounts of ethanol.

The processes disclosed herein have, among their many advantages, the ability to produce a product that is substantially identical to geologic petroleum in that it is compatible with existing petroleum infrastructure and can be refined into the same classes of compounds as those obtained from the refining of fossil fuels. Thus, the product resulting from the disclosed processes can be further refined into, among other things, jet fuel, aviation fuel (avgas), diesel fuel, gasoline, fuel oil and lubricating oil.

Jet fuels, such as Jet-A, Jet-A1 and JP-8, are a middle distillate that contains a mixture of straight and branched chain alkanes, aromatics and cycloalkanes having a chain length of between 10 to 14 carbons. Jet fuels are further characterized by a high energy density and the ability to remain liquid at very low temperatures.

Diesel fuel is composed of $C_8$ to $C_{21}$ hydrocarbons. Diesel is more energy dense than gasoline producing approximately 139,000 BTU/US gal when burned as opposed to 125,000 BTU/US gal for gasoline. Diesel fuel is characterized by its Cetane Index which is a measure of the fuel's propensity to auto-ignite under pressure. In the Cetane Index, cetane (n-hexadecane) is given a value of 100. Branched and aromatic molecules have a lower Cetane Index, hut diesel fuel typically contains around 25% aromatic hydrocarbons to provide for good flow properties at lower temperatures.

Gasoline typically is made up of $C_4$ to $C_{12}$ alkanes, isoalkanes and aromatics. Gasoline is characterized by its Octane Number which is a measure of the fuel's ability to resist pre-detonation. In the Octane Number system, 2,2,4-trimethylpentane has an Octane Number of 100 while n-octane has a value of 0.

The term fuel oil encompasses a large variety of oils used in furnaces or boilers to generate heat and in internal combustion engines to generate power. Fuel oil is placed in 6 classes based on chain length and boiling point. Nos. 1 to 3 fuel oils (Nos. 1-3 diesel) contain hydrocarbons in the $C_9$ to $C_{20}$ range. Heavier fuel oils, Nos. 4-6, are made up of $C_{12}$ to $C_{70}$ hydrocarbons.

Aviation fuel (avgas) is typically 75 to 90% isooctane with the remainder being made up of toluene and $C_4$ to $C_5$ paraffins. The Octane rating of aviation fuel is generally equal to or greater than 100. Aviation fuel is very similar to gasoline used in automobiles, but is usually more uniform in composition and, unlike automotive gasoline, often con brains lead as an anti-knock additive.

Although the present process has been exemplified using microalgae, particularly green and blue-green algae (cyanobacteria), it should be appreciated that the process is applicable to any biomass. For example, and without limitation, the present process can be applied to vascular plants in general and terrestrial vascular plants in particular. Thus, in one aspect, the biomass may be processed to reduce the particle size of the biomass to one that is suitable for pumping. The size reduction may be accomplished using any method known in the art, for example, by pulping or grinding. Prior, during or after grinding, water may be added to the biomass to produce a slurry that can be readily moved using pumps. Typically, the slurry will contain at least 50% water. In other cases the slurry may contain at least 60%, at least 70%, at least 80%, at least 90%, at least 95% or at least 99% water. As will be apparent to one of skill in the art, when the biomass comprises a microorganism, such as a microalga or cyanobacterium, it may not be necessary to reduce the particle size prior to extraction.

In some instances a dried biomass may be used. In such instances it may be advantageous to add a liquid such as water to the dried biomass to allow for pumping. The liquid may be added to produce a slurry containing about 50%, about 40%, about 30%, about 20%, about 15%, about 10%, about 5% biomass or about 1% biomass.

In one embodiment, the oleaginous compound produced by the processes described herein is recovered from biomass comprising a microorganism. The microorganism can be a prokaryote or a eukaryote. In some embodiments the microorganism is a photosynthetic organism, such as a green alga or a cyanobacterium (blue green alga). In other embodiments, the microorganism is an aquatic organism. In certain embodiments, the microorganism is photosynthetic and aquatic. Any microorganism containing one or more lipids or lipid-dike molecules can be used in the present processes.

in some embodiments, the oleaginous compound is recovered from an alga, for example, a green alga, a red alga, or a brown alga. In certain embodiments, the alga is a microalga, for example and without limitation, a *Chlamydamonas* ssp., *Dunaliella* ssp., *Haematococcus* spp., *Scenendesmus* spp., *Chlorella* spp. or *Nannochloropsis* spp. More particular examples, include, without limitation, *Chlamydomonas reinhardtii, Dunaliella salina, Haematococcus pluvialis, Scenedesmus dimorphus, D. viridis,* and *D. tertiolecta*. Examples of organisms contemplated for use herein include, but are not limited to, rhodophyta, chlorophyta, heterokontophyta, tribophyta, glaucophyta, chlorarachniophytes, euglenoids, haptophyta, cryptomonads, dinoflagellata, and phytoplankton. In other embodiments the oleaginous compound is extracted from a photosynthetic bacterium, for example, but not limited to *Synechococcus* ssp., *Synechocystis* ssp. *Athrospira* ssp., *Prochlorococcus* ssp., *Chroococcus* ssp., *Gleoecapsa* ssp., *Aphanocapsu* ssp. *Aphanothece* ssp., *Leptolyngbya* ssp., *Merismopedia* ssp., *Microcystis* ssp., *Coelosphaeritan* ssp., *Prochlorothrix* ssp., *Oscillatoria* ssp., *Trichodesmium* ssp., *Spirulina* ssp., *Microcoleus* ssp., *Chroococcidiopisis* ssp., *Anahaena* ssp., *Aphanizamenon* ssp., *Clyindrospermopsis* ssp., *Cylindrospermum* ssp., *Tolypothrix* ssp, or *Scytonema* ssp.

The microorganism may be grown under conditions which permit photosynthesis, however, this is not a requirement (e.g., the organism may be grown in the absence of light), in some instances, biomass can be obtained from an organism that has been genetically modified. In instances where biomass is obtained from a genetically modified microorganism, the microorganism may be genetically modified in such a way that photosynthetic capability is diminished or destroyed. In growth conditions where a microorganism is not capable of photosynthesis (naturally or due to genetic modification), the organism will be provided with she necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or any organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

The microorganism can be grown on land, for example, in ponds, aqueducts, landfills, or in closed or partially closed bioreactor systems. The microorganisms can also be grown directly in water, for example, in an ocean, sea, lake, river, reservoir, etc. In embodiments where the microorganism is mass-cultured, the organism can be grown in high density bioreactors using methods known in the art. For example, algae can be grown in high density photobioreactors (see, e.g., Lee et al, *Biotech. Bioengineering* 44:1161-1167, 1994) and other bioreactors (such as those for sewage and waste water treatments) (e.g., Sawayama et al, *Appl. Micro. Biotech.*, 41:729-731, 1994). In some embodiments, algae may not be mass-cultured primarily for its oil content but, for example, to remove heavy metals (e.g., Wilkinson, *Biotech. Letters*, 11:861-864, 1989), produce hydrogen (e.g., U.S. Patent Application Publication No. 20030162273), or to produce nutritional supplements or therapeutic compounds (Walker et al., *Plant Cell Rep.* 24:629-641, 2005).

The disclosed processes can be used to extract lipids, fats, terpenes, hydrocarbons or other oleaginous compositions from biomass and in particular aquatic microorganisms. The aqueous environment containing the microorganisms can be water from any natural source without treatment and/or without supplementation. The water can be fresh water, brackish water, or sea water. In some embodiments the aqueous environment may contain 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, etc.) may also be present in the aqueous environment. Thus an alternative method of measuring water quality is total dissolved solids (TDS). TDS is well known in the area of water quality and is a measure of the combined content of organic and inorganic substances dissolved in the water. In general, fresh water has a TDS of less than 1500 mg/l, brackish water has a TDS of from 1500 to 5000 mg/l and saline water has a TDS of greater than 5000 mg/l. Thus, in some embodiments, the aqueous environment can have TDS of up to 1500 mg/l, 2,000 mg/l, 2500 mg/l, 3000 mg/l, 3500 mg/l, 4000 mg/l, 4500 mg/l, 5000 mg/l, 5500 mg/l, 6000 mg/l, 6500 mg/l, 7000 mg/l, 7500 mg/l, 8000 mg/l, 8500 mg/l, 9000 mg/l, 10000 mg/l, 10500 mg/l, 11000 mg/l, 11500 mg/l, 12000 mg/l, 12500 mg/l, 13000 mg/l, 13500 mg/l, 14000 mg/l, 14500 mg/l, or 15000 mg/l.

Another way to classify water is by salinity. Salinity is a measure of the total dissolved salts in water and is traditionally measured in parts per thousand (‰). In certain embodiments the aqueous environment has a salinity of less than 0.5‰, from 0.5 to 3‰, from 4 to 29‰ from 30 to 50‰ or greater than 50‰. In other embodiments, the aqueous environment may be water that is not from a natural source. That is, the water composition and/or chemistry may be modified to provide the desired environment for the growth of the microorganism. For example and without limitation, in one embodiment the salt concentration of the water may be increased or decreased. In another embodiment, the pH of the water may be raised or lowered. In still another embodiment, the concentration of $CO_2$ in the water may be increased.

In some embodiments, the aqueous environment containing the microorganism may be supplemented with nutrients. The supplemental material may be elemental in nature, for example, nitrogen, potassium, phosphorous, etc. delivered either in elemental form or in other forms such a nitrates, potassium salts, etc. In other embodiments, the aqueous environment is supplemented with energy sources such as simple sugars, complex carbohydrates, etc. Various water-based media are known in the art for growing microorganisms such as microalgae and cyanobacteria and can be utilized.

In still other embodiments, the aqueous environment is supplemented with compounds to protect that microorganism of interest from predator organisms or contaminating organisms. Such compounds include herbicides, pesticides, bactericides and bacteriostats, used alone or in combination. The organism which is being cultivated can be naturally resistant to the compounds, can be resistant to the compound due to introduction of a mutation can be genetically engineered to be resistant to the compound, or can be artificially selected for increased resistance to the compounds.

Although not required to carry out the processes described herein, in some embodiments, the water content of the biomass is reduced prior to conducting the extraction process. Non-limiting examples of methods for reducing the water content (dewatering) of feedstock comprising aquatic biomass, and in particular microorganisms include, flocculation, centrifugation and filtration. It will be apparent to one of skill in the art that one or more of these methods may be combined to accomplish dewatering. For example, flocculation may be combined with centrifugation and/or filtration.

One method of increasing the concentration of microorganisms is to flocculate or aggregate the organisms to facilitate removal from the aqueous environment. Flocculants or flocculating agents promote flocculation by causing colloids and other suspended particles e.g., cells) in liquids to aggregate, forming a floc. Flocculants are used in water treatment processes to improve the sedimentation of small particles. For example, a flocculant may be used in swimming pools or drinking water filtration to aid removal of microscopic particles which would otherwise cause the water to be cloudy and which would be difficult to remove by filtration alone.

Many flocculants are multivalent cations such as aluminum, iron, calcium or magnesium. These positively charged molecules interact with negatively charged particles and molecules to reduce the barriers to aggregation. In addition, many of these chemicals, under appropriate and other conditions such as temperature and salinity, react with water to form insoluble hydroxides which, upon precipitating, link together to form long chains or meshes, physically trapping small particles into the larger floc.

Flocculation of microorganisms such as microalgae and cyanobacteria using chemical flocculants is well known in the water treatment arts. Long-chain polymer flocculants, such as modified polyacrylamides, are commercially available. These are supplied in dry or liquid form for use in the flocculation process. One of the most common flocculants, liquid polyacrylamide, is typically supplied as an emulsion with 10-40% actives and the rest is a carrier fluid, surfactants and latex.

An alternative to chemical flocculation is biological flocculation. In biological flocculation, the microorganism may be genetically engineered to produce one or more flocculation moieties on its surface. The flocculation moieties can be expressed constitutively or expression can be induced, for example, by the use of an inducible promoter. The flocculation moiety can be, for example, a carbohydrate or protein binding moiety that binds to a surface protein or carbohydrate located on the external surface of the microorganism. In such a case, expression of the flocculation moiety causes the microorganisms to bind to each other to form floc. In other non-limiting examples the population of microorganisms contains sub-populations of microorganisms that have been genetically engineered to express complementary flocculation moieties on their surfaces, for example a carbohydrate binding lectin and its corresponding carbohydrate or an antibody and its corresponding antigen. Flocculation can be induced by growing the two populations separately and then mixing them, or alternatively, inducing expression of one or both of the molecules involved in flocculation. In another example, an organism that is genetically modified to produce and secrete a flocculation moiety can be used. Further examples of biological flocculation can be found in International Patent Application Publication WO 2009/158658.

In another embodiment, dewatering can be achieved by filtration, for example by membrane filtration. In this method, water permeates through the membranes and the microorganisms become more concentrated on one side of the membranes. Typically, the membranes operate under a slight vacuum induced by a permeate pump, which pumps away water that flows through the membrane. Compressed air may be fed to the bottom of the membrane module to prevent solids from accumulating on the outside surface of the membranes. The air also provides agitation that keeps the microorganisms suspended. Permeate water is also periodically pumped in reverse (from the inside to the outside of the membrane) to remove any particles that may be lodged in the membrane interstices.

Additionally, dewatering may be accomplished by centrifugation. As is known in the art, a centrifuge uses rotation around a fixed axis to generate centripetal acceleration resulting in the separation of materials based on density. Separation using centrifugation can be accomplished in a batch or continuous process. Typically, a continuous process is used for large volumes. In one embodiment a disc stack centrifuge is used. In another embodiment, a decanter centrifuge is used. Disc stack and decanter centrifuges are well known in the art and commercially available from a number of manufacturers. Centrifugation may be applied to untreated material or used in combination with additional dewatering processes such as flocculation and/or filtration. By way of example and not limitation, material may be first subjected to flocculation followed by centrifugation of the floc resulting in biomass having a water content of about 75%, about 80%, about 85%, about 90%, about 95% or about 99%.

In one embodiment, the feedstock comprising biomass is subject to a pretreatment. The feedstock may be any biomass such as those described herein, and in particular a microorganism, such as an aquatic microorganism. In particular embodiment, the biomass comprises one or more alga or cyanobacterium. The feedstock used in the pretreatment may contain about 50%, about 60%, about 70%, about 80%, about 85%, about 90%, about 95% or about 99% water. During the pretreatment, the biomass is heated to a pretreatment temperature between about 80° C. and about 220° C. In certain embodiments the pretreatment temperature is between about 100° C. and 210° C., between about 160° C. and 200° C. or between about 170° C. and 210° C. In particular embodiments the pretreatment temperature is between about 180° C. and 200° C. The material may be held at the pretreatment temperature from between about 5 minutes and 60 minutes. In certain embodiments, the feedstock is held at the pretreatment temperature for between about 20 minutes to 40 minutes. As will be appreciated by those skilled in the art, equivalent pretreatments may be obtained with various combinations of time and temperature. For example, as temperature is increased, the amount of time required may decrease. In particular embodiments, pretreatment of the biomass comprises heating to between about 170° C. and 210° C. for between about 20 minutes to 40 minutes; to between about 160° C. and about 180° C. for between about 30 minutes and 60 minutes; and between about 180° C. and 200° C. for between about 25 minutes and 35 minutes.

In some embodiments, the feedstock (biomass) is subjected to mixing during the pretreatment, while in other embodiments no mixing is used. When mixing is utilized, it can be intermittent or constant. The mixing can be accomplished by any method known in the art. In one embodiment, mixing is accomplished using an impeller, rotor or paddle. In another embodiment, mixing is achieved by use of a pump. Other methods of mixing the feedstock will be readily apparent to those of skill in the art.

in some embodiments, acid is added to the feedstock during pretreatment. If used, the acid may be added prior to or during heating the material to the pretreatment temperature. Addition of the acid, may result in the feedstock having a pH of between about 3 and 6. In certain embodiments the biomass will be acidified to a pH of about 3, about 4, about 5 or about 6 during the pretreatment process. Any acid may be used in the pretreatment process. In some embodiments, a strong acid such as HI, $H_2SO_4$, HBr, HCl, $H_3PO_4$, $HNO_3$ or $CH_3SO_3H$ is used.

In some embodiments, liquid may be removed from the pretreated material. Removal of liquid may be achieved by any method known in the art, such as those described herein. For example following pretreatment, the material may be allowed to phase separate into at least a solids and liquid phase, and the phases separated by, for example decanting, siphoning, draining or pumping. In other embodiments, the liquid phase may be removed by filtration or centrifugation such as described herein. Exemplary methods of centrifugation include the use of stacked disc and decanter centrifuges.

In some embodiments, the pretreatment may further comprise rinsing the biomass. If rinsing is utilized, the rinse liquid, for example water, is added to the biomass following heating and removal of the liquid phase. The amount of rinse liquid used in rinsing may vary between 25% and 200% of the volume of the liquid phase removed following heating. In certain embodiments, rinsing involves mixing of the biomass and the added rinse liquid for between about 5 minutes and 60 minutes. In particular embodiments, the biomass and rinse liquid are mixed for between about 5 minutes and about 10 minutes, between about 10 minutes and about 20 minutes, between about 20 minutes and about 30 minutes, between about 25 minutes and about 30 minutes, between about 30 minutes and 40 minutes, between about 40 minutes and about 50 minutes, or between about 50 minutes and about 60 minutes. After mixing, the added rinse liquid may be removed using any of the methods described herein including gravity separation, centrifugation and filtration.

Following pretreatment, the pretreated feedstock may be processed further to obtain oleaginous compounds or it may be stored. If the material is stored, it may be stored for any time period ranging from 1 day to 1 year. For example, the pretreated feedstock may be stored for a period from 1 day to 1 month, from 1 month to 3 months, from 3 months to 6 months, from 6 months to 9 months or from 9 months to 12 months. The pretreated feedstock may be stored at ambient temperature or it may be stored at a controlled temperature. If the material is stored at a controlled temperature, the storage temperature may be between 0° C. and ambient temperature. In certain embodiments, the storage temperature can be between about −20° C. and about −10° C., between about −10° C. and about −5° C., between about −5° C. and about 0° C., between about 0° C. and about 5° C., between about 5° C. and about 10° C., between about 10° C. and about 15° C., between about 10° C. and about 20° C., between about 15° C. and about 20° C., or between about 20° C. and about 25° C.

The pretreated feedstock may be stored in an open container, a container that is covered but open to the atmosphere, or a closed container (i.e. not open to the atmosphere). If a closed container is utilized, there may be a headspace, that is, the space between the top of the stored material and the top of the container. If such a headspace is present, the atmosphere in the headspace can be air or some artificial atmosphere. For example, the atmosphere in the headspace may contain an inert gas such as nitrogen, carbon dioxide or argon. In certain embodiments the atmosphere in the headspace may be maintained at a pressure greater or lesser than normal atmospheric pressure.

In one embodiment the feedstock comprising biomass and water is subject to hydrothermal treatment or processing (HTT) and in particular hydrothermal liquefaction, with or without prior pretreatment. In one embodiment, the feedstock is an aqueous slurry containing biomass. In another embodiment, the feedstock is an aqueous medium containing a microorganism, for example a microalga or a bacterium. In certain embodiments, the microorganism is a photosynthetic microorganism such as a photosynthetic alga or a cyanobacterium (blue green alga). The feedstock will typically, but not necessarily, contain about 50%, about 60%, about 70%, about 80%, about 85%, about 90%, about 95% or about 99% water. In certain, embodiments, a liquid, for example water, may be added to the feedstock to increase the moisture content. For example, if dried, pretreated and/or stored feedstock is used, liquid may be added.

The feedstock is introduced into a closed reaction vessel. The feedstock can be introduced by any suitable method, but is typically introduced using a pipe. The feedstock can be moved into the reaction chamber using known techniques. In one embodiment the feedstock is moved by the use of pumps, while in other embodiments gravity flow is used.

In the hydrothermal treatment, the initial feedstock is heated to a hydrothermal processing temperature of between about 180° C. and about 600° C. or between about 250° C. and about 500° C. In certain embodiments the hydrothermal processing temperature is between about 250° C. and about 370° C. In other embodiments the initial feedstock is heated to a temperature between about 250° C. and about 270° C. In still other embodiments, the initial feedstock is heated to a temperature between about 270° C. and about 330° C., between about 280° C., and about 320° C., or between about 290° C. and about 310° C. In additional embodiments, the initial feedstock is heated to a temperature of about 250° C., about 260° C., about 270° C., about 280° C., about 290° C., about 300° C., about 310° C., about 320° C., about 330° C., about 340° C., about 350° C., about 360° C., about 375° C., about 400° C., about 425° C., about 450° C., about 475° C. or about 500° C. In one embodiment, the initial feedstock is rapidly heated to the final temperature, for example, over a period of about 5 minutes, about 10 minutes, about 15 minutes, about 20 minutes, about 30 minutes, about 40 minutes, about 50 minutes, or about 60 minutes. The initial feedstock may be held at the hydrothermal processing temperature for a period of between about 0 minutes (i.e. no hold time) and about 15 minutes, about 30 minutes, about 60 minutes, about 90 minutes, about 2 hours, about 3 hours or about 4 hours. In other embodiments, the feedstock is held at the hydrothermal processing temperature for from about 10 minutes to about 30 minutes, from about 30 minutes to about 90 minutes or from about 90 minutes to about 120 minutes. In certain embodiments, the initial feedstock is held at the hydrothermal processing temperature for 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes or about 240 minutes.

The hydrothermal processes can be carried out with or without the use of a catalyst. Catalysts that may be used include $Fe(CO)_5$—S, $Na_2CO_3$, and KOH. $Fe(CO)_5$—S may be used at a concentration of from 0 to 1 mmol. $Na_2CO_3$ and KOH can be used at a concentration of from 0 to 1.0 M.

In some embodiments, the feedstock is subjected to mixing during the hydrothermal processing, while in other embodiments no mixing is used. When mixing is utilized, it can be intermittent or constant. The mixing can be accomplished by any method known in the art. In one embodiment, mixing is accomplished using an impeller, rotor or paddle. In another embodiment, mixing is achieved by use of a pump. Other methods of mixing the feedstock will be readily apparent to those of skill in the art.

Also during the hydrothermal processing the pressure within the reaction vessel increases due to the heating of the contents of the vessel. The pressure during the process need not be held at a particular level, but is maintained at a pressure high enough to prevent vaporization (phase change or boiling) of the liquid in the vessel and below the pressure rating of the reaction vessel. During hydrothermal processing, excess gas may be vented from the reaction vessel. Venting may be continuous or intermittent. For example, gas may be vented about every 5 minutes, every 10 minutes, every 15 minutes, every 20 minutes, every 25 minutes or every 30 minutes. As is well known in the art, the point at which there is phase change from a liquid to a vapor (e.g. boiling point) is affected by both temperature and pressure. It is well within the ability of the skilled artisan to determine the minimum pressure that must be maintained to prevent a phase change at any given temperature.

The vented gas which often contains high levels of $CO_2$ can be vented to the atmosphere or the gas can be captured and used for other purposes. In one embodiment, the $CO_2$ produced is captured and utilized for growing additional biomass, in another embodiment, ammonia gas produced is captured and used as a source of nitrogen for growing additional biomass.

In some embodiments, the headspace in the hydrothermal processing reaction vessel contains an inert gas such as nitrogen, argon or carbon dioxide. In other embodiments the headspace contains air. In certain embodiments, the headspace initially contains air or an inert gas, but during the hydrothermal processing the initial gas in the headspace is displaced by gases emitted from the feedstock during the hydrothermal processing.

In some embodiments, the hydrothermal processing is carried out as a batch process. That is, an amount of feedstock is added to the hydrothermal processing reaction vessel, the hydrothermal process completed, and the contents of the reaction vessel removed. In other embodiments, a continuous process is used. In the continuous process, new feedstock is added and hydrothermal process product is removed on a continuing basis. The addition of feedstock and removal or product may be intermittent or it may be continuous. An example of a continuous process configuration can be seen in FIG. 1.

The product of the hydrothermal treatment or processing is then cooled to a temperature between ambient temperature and about 150° C. In certain embodiments, the hydrothermal processing product is cooled to a temperature between about 30° C. and about 150° C., between about 30° C. and about 120° C., between about 100° C. and about 150° C., between about 110° C. and about 130° C., between about 50° C. and about 70° C. or between about 55° C. and about 65° C. In other embodiments, the product of the hydrothermal processing cooled to a temperature of about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C. and about 150° C.

Following cooling, the hydrothermal processing product is acidified to a pH between about 2.0 and about 6.0, between about 2.0 and about 3.0, between about 3.0 and about 4.0, between about 4.0 and about 5.0, between about 3.5 and about 4.5, between about 3.6 and about 4.4, between about 3.7 and about 4.5, between about 3.8 and about 4.6, between about 3.9 and about 4.7, between about 4.0 and about 4.8, between about 4.5 and about 5.0, between about 5.0 and about 5.5 or between about 5.5 and about 6.0. In other embodiments, the cooled product of the hydrothermal processing is acidified to a pH of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In still other embodiments, the product of hydrothermal processing is acidified to a pH from about 2.0 to less than 6.0, from about 3.0 to less than 6.0 or from about 4.0 to less than 6.0. Any acid may be used in the acidification process. In some embodiments, a strong acid such as HI, $H_2SO_4$, HBr, HCl, $H_3PO_4$, $HNO_3$ or $CH_3SO_3H$ is used. The acidification process is typically, but not necessarily, carried out at atmospheric pressure, with mixing. Alternatively, the acidification process is carried out at the vapor pressure of the solution containing water, biomass, acid and solvent. Acidification following, rather than before or during hydrothermal processing has several advantages. Thus in one embodiment, the biomass is not acidified (i.e. there is no addition of acid) prior to or during hydrothermal processing. In another embodiment there is no addition of acid following pretreatment or during hydrothermal processing. One advantage of addition of the acid after, rather than before or during hydrothermal processing, is significantly less acid degradation occurs and so less acid is used in the process without a significant decrease in yield. In addition, acidification following hydrothermal processing results in a final product having in fewer impurities.

The acidified product may be held at a temperature of between about 40° C. and about 150° C., between about 40° C. and about 70° C., between about 70° C. and about 100° C., between about 100° C. and about 130° C., or between about 130° C. and about 150° C. In other embodiments, the acidified product is heated to about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C. The hold time may range from 1 minute to about 240 minutes, from 1 minute to 45 minutes, from 1 minute to about 5 minutes, from 5 minutes to about 10 minutes, from about 10 minutes to about 50 minutes, from 15 minutes to about 45 minutes, from about 20 minutes to about 40 minutes, or from about 25 minutes to about 35 minutes. In certain embodiments, the hold time may range from 0 minutes (no hold time) to about 1 minute, about 5 minutes, about 20 minutes, about 30 minutes, about 45 minutes, about 60 minutes, about 120 minutes or about 240 minutes. In other embodiments, the hold time is less than 5 minutes, about 1 minute, about 5 minutes, about 10 minutes, about 15 minutes, about 20 minutes, about 25 minutes, about 30 minutes, about 35 minutes, about 40 minutes, about 45 minutes, about 60 minutes, about 90 minutes, about 120 minutes, about 150 minutes, about 180 minutes, about 210 minutes, or about 240 minutes. During the hold period, the acidified product may optionally be mixed. Any method of mixing known in the art, including those discussed herein, may be used. Alternatively, the acidification may be achieved using an on-line mixer with no hold time.

Following the acid treatment, at least one solvent may be added to the acidified product to produce a solvent extraction composition. Optionally, prior to the addition of solvent, the pH of the material is determined and if necessary the pH adjusted that which existed prior to heating. In one embodiment, an amount of solvent approximately equal in volume to the volume of water present in the acidified product is added to produce a solvent extraction composition. In other embodiments the ratio of solvent to water in the acidified product is 0.1:1, 0.2:1, 0.3:1, 0.4:1, 0.5:1, 0.6:1, 0.7:1, 0.8:1, 0.9:1, 1.1:1, 1.2:1, 1.3:1, 1.4:1 or 1.5:1. Any solvent suitable for the extraction of oleaginous compounds may be used, including, but not limited to acetonitrile, ethanol, methyl-t-butyl ether (MTBE), methyl ethyl ketone (MEK), propanol, isopropyl alcohol (IPA), methanol, cyclohexane, heptane, toluene (methylbenzene), chloroform (trichloromethane), methylene chloride (dichloromethane) and methyl isobutyl ketone (MIBK). The solvent can be a polar solvent, a non-polar solvent, or a combination of polar and non-polar solvents. In one embodiment, any organic solvent with a low solubility in water or which is sparingly soluble in water, but in which lipids and other oleaginous compounds are soluble or substantially soluble can be used. In another embodiment, the solvent is one which is immiscible in water, but one in which lipids and other oleaginous compounds are miscible. Non-limiting examples of suitable solvents include hexane, cyclohexane, heptane, toluene (methylbenzene), chloroform (trichloromethane), methylene chloride (dichloromethane) and methyl isobutyl ketone (MIBK). Suitable solvents can be used alone or in combinations. In one embodiment, the ratio of biomass to water to solvent is 1:10:10. In other embodiments, the ratio of biomass to water to solvent is ratios are 1:1:1, 1:2:2, 1:3:3, 1:4:4, 1:6:6, or 1:8:8 The solvent extraction composition is heated in a closed extraction vessel to an extraction temperature between about 20° C. and about 150° C., between about 90° C. and about 150° C., between about 100° C. and about 140° C., between about 110° C. and about 130° C., between about 50° C. and about 90° C., between about 60° C. and about 80° C., or between about 65° C. and about 75° C. In other embodiments, the solvent extraction composition is heated to an extraction temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C. or about 150° C. The solvent extraction composition is held at the extraction temperature for between about 1 minute and about 240 minutes, between about 10 minutes and about 50 minutes, between about 15 minutes and about 45 minutes, between about 20 minutes and about 40 minutes, or between about 25 minutes and about 35 minutes. In other embodiments, the solvent extraction composition is held at the extraction temperature for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes, or about 240 minutes. As discussed above, as the temperature increases, the pressure within the extraction vessel also increases. The pressure within the extraction vessel need not held at any particular level, but is maintained such that the liquids in the extraction vessel do not vaporize (undergo a phase change). During the process the solvent extraction composition is optionally mixed. If mixing is utilized it can be intermittent or constant. The mixing can be accomplished by any method known in the art. In one embodiment, mixing is accomplished using an impeller, rotor or paddle. In another embodiment, mixing is achieved by use of a pump. In some embodiments, a combination of mixing methods is used, for example, a pump in combination with an impeller. Other methods of mixing the feedstock will be readily apparent to those of skill in the art.

After the solvent extraction composition has been held at the extraction temperature for the desired period of time, the mixing (if used) and heating is discontinued and the organic phase or phases separated from the aqueous phase. Separation of the organic and aqueous phases can take place in the extraction vessel or the solvent extraction composition can be transferred to another vessel. In one embodiment the pressure in the extraction vessel is lowered to atmospheric pressure. In one embodiment, the solvent extraction composition is allowed to cool to a temperature between the extraction temperature and ambient temperature.

Any suitable method of achieving phase separation can be used. In one embodiment, separation between the organic and aqueous phases is achieved by centrifugation, either batch or continuous. Methods of separating liquid phases by centrifugation are well known in the art. In one embodiment, phase separation is achieved using a stacked disc centrifuge. In another embodiment, phase separation is achieved using a decanter centrifuge. In still another embodiment, gravity separation is used. In this embodiment, the solvent extraction composition is allowed to stand without mixing for a period of time to allow for separation into phases. It is also possible to combine centrifugation with gravity separation. For example and without limitation, gravity separation can be used to separate the liquid and particulate phases, and then the liquid phase further separated into the aqueous and organic phases using centrifugation.

Regardless of the method used, typically the solvent extraction composition will separate into at least an aqueous phase and an organic phase or miscella containing the oleaginous compound(s) or oil. In some embodiments, there may be at least three phases, a particulate phase, an aqueous phase and an organic phase or miscella. When mixtures of solvents are used, there may be more than one organic phase present. In addition, in some embodiments there may be an emulsion phase between the aqueous phase and the organic phase(s). As part of the separation process, the organic phase(s) is removed from the aqueous phase and, if present, the particulate phase. When gravity separation or batch centrifugation is used, the miscella can be removed by any method that results in minimal re-mixing of the phases. For example, and without limitation, the miscella can be removed by pouring, pumping, gravity flow or siphoning. When gravity separation is used, the removal of the miscella can be continuous or intermittent, in continuous gravity separation, solvent extraction composition is continuously added to the separation vessel and an equal amount of miscella continuously removed. When continuous centrifugation is used, the separated phases are continuously removed from the centrifuge and collected. The collected phases from continuous centrifugation can be subjected to further separation steps, such as additional centrifugation, if so desired.

Optionally, the separated aqueous phase is returned to a solvent extraction vessel and a volume of fresh solvent is added to produce a secondary solvent extraction composition. The fresh solvent can be solvent recovered from previous extractions, new solvent or a combination of new and recovered solvent. Thus, in some embodiments fresh solvent contains less than 10%, less than 5%, less than 2%, less than 1%, less than 0.5%, less than 0.25% or less than 0.1% of material from the extracted biomass. In one embodiment, the volume of fresh solvent added is equal to the volume of the aqueous phase. In another embodiment, the volume of fresh solvent added is equal to the volume of the organic phase removed from the separated aqueous phase. The secondary solvent extraction composition subjected to the solvent extraction and phase separation processes described above. This re-extraction of the aqueous phase and/or residual biomass can be carried out several times, for example 2 times, 3 times, 4 times, 5 times, 6 times or more. In one embodiment, a counter current system is used in which the organic phase or miscella from the re-extraction of the aqueous phase is used to provide some or all of the solvent in the first extraction.

The miscella obtained from the solvent extraction is treated to separate the solvent from the oleaginous compound(s). In one embodiment, solvent removal is by way of distillation. In this embodiment, the miscella is heated to a temperature sufficient to cause vaporization of the solvent, but lower than the vaporization temperature of the oleaginous compound(s) of interest. The vaporized solvent is recovered by condensation and collection. In one embodiment, the recovered solvent is reused in the solvent extraction process.

Following solvent removal, the oleaginous compound may be further concentrated by the use of one of more additional solvent removal processes. In one embodiment, such further concentration is achieved by a secondary distillation, adsorption, and/or centrifugation.

It should be appreciated that solvent extraction following hydrothermal treatment and acidification is optional. Thus, in some embodiments, the aqueous and organic phases may be separated using any of the method described herein without the use of a solvent. For example and without limitation, following hydrothermal treatment, with or without acidification, the treated material can be allowed to separate into at least an aqueous and an organic phase without the use of a solvent.

In certain embodiments, the oleaginous compound(s) obtained from biomass by the processes described herein have a calcium content of less than 100 ppm, 90 ppm, 80 ppm, 70 ppm, 60 ppm, 50 ppm, 40 ppm, 30 ppm, 20 ppm, 10 ppm or 5 ppm. In other embodiments, the oleaginous compound(s) obtained from biomass have a magnesium content of less than 100 ppm, 90 ppm, 80 ppm, 70 ppm, 60 ppm, 50 ppm, 40 ppm, 30 ppm, 20 ppm, 10 ppm or 5 ppm. In additional embodiments the oleaginous compound(s) obtained from biomass by the processes described herein have a manganese content of less than 100 ppm, 90 ppm, 80 ppm, 70 ppm, 60 ppm, 50 ppm, 40 ppm, 30 ppm, 20 ppm, 10 ppm, 5 ppm or 1 ppm. In still other embodiments, the oleaginous compound(s) obtained from biomass by the processes described herein have a phosphorus content of less than 100 ppm, 90 ppm, 80 ppm, 70 ppm, 60 ppm, 50 ppm, 40 ppm, 30 ppm, 20 ppm or 10 ppm. In further embodiments, the oleaginous compound(s) obtained from biomass by the processes described herein have a sodium content of less than 100 ppm, 90 ppm, 80 ppm, 70 ppm, 60 ppm, 50 ppm, 40 ppm, 30 ppm, 20 ppm, 10 ppm, 5 ppm or 1 ppm. In yet additional embodiments, the oleaginous compound(s) obtained from biomass by the processes described herein have a strontium content of less than 50 ppm, 40 ppm, 30 ppm, 20 ppm, 10 ppm, 5 ppm, 1 ppm, or 0.01 ppm.

The recovery process described herein can be conducted in a batch mode, semi batch mode or in a continuous mode. When a batch mode is used, each of the individual processes within the overall recovery process is carried out as a discreet operation. In a semi batch mode, some processes are carried out in batch mode while a continuous mode is used for other processes. When a continuous mode is used, material continually moves through each aspect of the recovery process. When a continuous mode is used, a countercurrent method may be employed. An exemplary illustration of a continuous, countercurrent embodiment of the recovery process described herein is presented in FIG. 1. In the example, biomass, in the form of an algal slurry, is heated to the desired temperature. The algal slurry may be anywhere from 1% to 50% w/v algae. For example the algal slurry may be 1%, 2%, 3%, 4%, 5%, 6%, 7%, 8%, 9%, 10%, 15%, 20%, 30%, 40% or 50% algae w/v. Heating may be accomplished by the use of heat exchangers, heaters or a combination of heat exchanges and heaters. In reference to the exemplary process depicted in FIG. 1, the algal biomass is heated using a series of heat exchanges 101 and 102. In 101, heat is exchanged between the incoming slurry and the hot raffinate from the solvent extraction process, while in 102, heat is exchanged between the incoming shiny and the material exiting the hydrothermal reactor unit 104. If the slurry has not reached the desired temperature through heat exchange, the temperature can be further increased using a heater 103, for example a trim heater. The temperature of the slurry can be increased to between about 180° C. and about 600° C. or between about 250° C. and about 500° C. In certain embodiments, the temperature of the shiny can be increased to between about 250° C. and about 70° C. in other embodiments the slurry is heated to a temperature between about 250° C. and about 270° C. In still other embodiments, the slurry is heated to a temperature between about 270° C. and about 330° C., between about 280° C. and about 320° C., or between about 290° C. and about 310° C. In additional embodiments, the slurry is heated to a temperature of about 250° C., about 260° C., about 270° C., about 280° C., about 290° C., about 300° C., about 310° C., about 320° C., about 330° C., about 340° C., about 350° C., about 360° C. about 375° C., about 400° C., about 425° C., about 450° C., about 475° C. or about 500° C. In one embodiment, the slurry is rapidly heated such that it reaches the hydrothermal processing temperature in not more than about 0.5 minutes, not more than about 10 minutes, not more than about 15 minutes, not more than about 20 minutes, not more than about 25 minutes, not more than about 30 minutes, not more than about 35 minutes, not more than about 40 minutes, not more than about 45 minutes, not more than about 50 minutes, not more than about 55 minutes or not more than about 60 minutes.

The heated slurry is held at the desired temperature, under pressure, in a hydrothermal reactor 104 for a time sufficient to complete the hydrothermal treatment. In one embodiment, the pressure within the hydrothermal reactor is not held at a specific value hut is allowed to vary between a pressure sufficient to prevent (phase change) of the liquid in the material being treated and the maximum pressure rating of the hydrothermal reactor 104, in other embodiments, hydrothermal processing is carried out at a specific pressure, for example, between about 1 MPa and 30 MPa, between about 2 MPa and about 10 MPa, or between about 3 MPa and about 5 MPa. In other embodiments, the hydrothermal processing is carried out at a pressure of about 1 MPa, about 2 MPa, about 3 MPa, about 4 MPa, about 5 MPa, about 6 MPa, about 7 MPa, about 8 MPa, about 9 MPa, about 10 MPa, about 11 MPa, about 12 MPa, about 13 MPa, about 14 MPa, about 15 MPa, about 16 MPa, about 17 MPa, about 18 MPa, about 19 MPa, about 20 MPa, about 21 MPa, about 22 MPa, about 23 MPa, about 24 MPa, about 25 MPa, about 26 MPa, about 27 MPa, about 28 MPa, about 29 MPa or about 30 MPa. The time the slurry is held in the hydrothermal reactor 104 can be between 0 minutes (i.e. no hold time) and about 240 minutes or between about 10 minutes and about 20 minutes. In certain embodiments, the slurry is held at the hydrothermal processing temperature for about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes or about 240 minutes.

Upon exiting the hydrothermal reactor unit 104, the hydrothermal processing product enters a cooling unit 105 where the product is cooled to a temperature between ambient temperature and about 150° C. The cooling can be accomplished using a heat exchanger, by flashing the liquid or a combination of both. In certain embodiments, the hydrothermal processing product is cooled to a temperature between about 30° C. and about 70° C. between about 70° C. and about 90° C., between about 90° C. and about 110° C., between about 110° C. and about 130° C. or between about 130° C. and about 150° C. in other embodiments, the product of the hydrothermal processing is cooled to a temperature of about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C. about 130° C., about 135° C., about 140° C., about 145° C. or about 150° C.

Upon exiting the cooling unit 105, the hydrothermal processing product can enter an outlet flash unit 106. In the outlet flash unit, volatile compounds vaporize and are condensed using a condenser unit 115. In one embodiment, flammable compounds in the condensate from the condenser unit 115 are burned as a source of energy. Upon exiting the flash unit 106, if necessary, the material can be heated in heating unit 107 to the temperature between about 50° C. and about 90° C., between about 90° C. and about 110° C., between about 110° C. and about 130° C. or between about 130° C. and about 150° C. In other embodiments, the material is heated to about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C. or about 130° C.

The heated material then enters the acidification unit 108. In the acidification unit 108, the pH of the material is adjusted to a pH between about 2.0 and 6.0, between about 3.0 and 4.0, between about 4.0 and about 5.0, between about 4.1 and about 4.9, between about 4.2 and about 4.8, between about 4.3 and about 4.7, between about 4.0 and about 4.5, between about 4.5 and about 5.0, between about 5.0 and about 5.5 or between about 5.5 and 6.0. In other embodiments, material is acidified to a pH of about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9 or about 6.0. In still other embodiments, the material is acidified to a pH from about 2.0 to less than 6.0, from about 3.0 to less than 6.0 or from about 4.0 to less than 6.0. Any acid may be used in the acidification process. In some embodiments, a strong acid such as HI, $H_2SO_4$, HBr, HCl, $H_3PO_4$, $HNO_3$ or $CH_3SO_3H$ is used. The material may be held in the acidification unit 108 for a period from 0 minutes (i.e. no hold time) to 240 minutes, from about 1 minute to about 5 minutes, from about 5 minutes to about 10 minutes, from about 10 minutes to about 20 minutes, from about 20 minutes to about 30 minutes, from about 30 minutes to about 40 minutes, from about 40 minutes to about 50 minutes, from about 50 minutes to about 60 minutes, from about 60 minutes to about 90 minutes, from about 90 minutes to about 120 minutes, from about 120 minutes to about 150 minutes, from about 150 minutes to about 180 minutes, from about 180 minutes to about 210 minutes, or from about 210 minutes to about 240 minutes. In certain embodiments, acidification may be achieved using an in-line mixer. In other embodiments, a hold time is less than 5 minutes, about 1 minute, about 5 minutes, about 10 minutes, about 15 minutes, about 20 minutes, about 25 minutes, about 30 minutes, about 35 minutes, about 40 minutes, about 45 minutes, about 55 minutes, about 60 minutes, about 90 minutes, about 120 minutes, about 150 minutes, about 180 minutes, about 210 minutes or about 240 minutes is used.

Upon exiting the acidification unit 108, the material enters a primary solvent extraction unit 109. In the primary solvent extraction unit 109 the acidified material is combined with a solvent to form a solvent extraction composition. As described herein, any organic solvent with a low solubility in water or which is sparingly soluble in water, but in which lipids and other oleaginous compounds are soluble or substantially soluble can be used. The solvent can be non-polar, polar or a combination of polar and non-polar solvents. Exemplary solvents include, but are not limited to, at least one of hexane, cyclohexane, heptane, toluene (methylbenzene), chloroform (trichloromethane), methylene chloride (dichloromethane) and methyl isobutyl ketone (MIBK). In this exemplary embodiment, at least part of the solvent used in the primary extraction unit 109 is in the form of miscella from one or more downstream separators. Additional solvent may also be provided in the form of new solvent or solvent recovered from miscella. The solvent extraction composition has an average residence time in the primary solvent extraction unit 109 of between about 1 minute and about 240 minutes, between about 10 minutes and about 50 minutes, between about 15 minutes and about 45 minutes, between about 20 minutes and about 40 minutes, or between about 25 minutes and about 35 minutes. In other embodiments, the solvent extraction composition is held at the extraction temperature for an average time of about 5 minutes, about 10 minutes, 15 minutes, about 20 minutes, about 25 minutes, about 30 minutes, about 35 minutes, about 40 minutes, about 45 minutes, about 50 minutes, about 55 minutes, about 60 minutes, about 90 minutes, about 120 minutes, about 150 minutes, about 180 minutes, about 210 minutes or about 240 minutes.

The temperature in the primary solvent extraction unit 109 is held between about 50° C. and about 70° C., between about 70° C. and about 90° C., between about 90° C. and about 110° C., between about 110° C. and about 130° C. or between about 130° C. and about 150° C. In other embodiments, the temperature is held at about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C. or about 150° C. Temperature in the primary solvent extraction unit 109 can be maintained by any method known in the art, for example, by using an insulated unit and/or a heat transfer liquid. The primary solvent extraction is conducted under pressure. The pressure within the primary solvent extraction unit 109 need not be controlled at a particular pressure, but is maintained such that the liquids in the extraction unit do not vaporize (undergo a phase change). During the process the solvent extraction composition may be optionally mixed, if used, the mixing can be intermittent or constant. The mixing can be accomplished by any method known in the art. In certain embodiments, mixing is accomplished using an impeller, rotor, paddle, pump or any combination thereof.

Material from the primary solvent extraction unit 109 then moves to the primary separator 110. In the primary separator, the extraction composition is separated into a least two phases, an organic phase or miscella and art aqueous phase or raffinate. In other embodiments, the extraction composition is separated into a least three phases, an organic phase or miscella, an aqueous phase or raffinate, and a particulate or solids phase. It will be apparent to one of skill in the art that additional phases may also be present. For example, when a mixture of solvents is used, the organic phase may further be separated into sub-phases. In one embodiment, separation is achieved by gravity separation in which the contents of the primary separator 110 are allowed to stand with no or minimal agitation or mixing for a time sufficient to allow the phases to separate. In another embodiment, the primary separator 110 is a mechanical decanter, for example a decanting centrifuge. High volume mechanical decanters for industrial applications are well known in the art and are available for purchase from a number of commercial sources.

The miscella (line M1) from the primary separator 110 is transferred to a solvent recovery unit 113, in the solvent recovery unit 113, the miscella is heated to a temperature above the vaporization point of the solvent or solvents, but below the vaporization point of the lipids, oils or oleaginous compounds of interest. The vapor comprising the solvent is then cooled to condense the vapor and recover the solvent in liquid form. The solvent so recovered can be directly reused in the solvent extraction process or it can be further purified prior to reuse. The recovered solvent can be used immediately or stored for future use. If a combination of solvents is used, more than one vaporization and/or condensation temperature may be employed to in order to fractionate the solvent into its various constitutes.

Following removal of the solvent(s), the remaining material may be transferred to a secondary solvent recovery unit 114. In the secondary solvent recovery unit 114, the material may be further concentrated by the use of one of more additional solvent removal processes. In one embodiment, such further concentration is achieved by a secondary distillation or adsorption. Upon completion of solvent recovery, the algal oil can be stored or shipped to a processor or refiner. The algal oil may be shipped by truck, rail car, pipeline, ship, barge or some combination thereof. In certain embodiments, the algal oil is subjected to further processing prior to storage and/or shipment. Such treatments, include, but are not limited to, hydrotreating, decarboxylation, decarbonylation, hydrodeoxygenation, isomerization (including hydroisomerization), desulfurization, denitrogenation, hydrocracking and/or catalytic cracking.

The aqueous phase or raffinate from the primary separator 110 is transferred to a secondary solvent extraction unit 111 for a second solvent extraction. The extraction process described for the primary solvent extraction unit 109 is repeated in a secondary solvent extraction unit 111. Material from the secondary solvent extraction unit 111 is transferred to a secondary separator 112. In the secondary separator 112, the material is separated into at least an organic phase or miscella and an aqueous phase or raffinate. In some cases a solids or particulates phase may also be present. As previously described, phase separation can be accomplished by gravity separation or by mechanical methods such as the use of a decanting centrifuge. The organic phase or miscella from the secondary separator (line M2) is transferred to back to the primary solvent extraction unit 109 where it is used in the primary solvent extraction process. The aqueous layer or raffinate and the solids are removed from the secondary separator 112.

Solids obtained from the recovery process described herein, if present, can be put to a variety of uses. In one embodiment, solids are transferred to one of more digesters. The digesters can be aerobic, anaerobic, or a combination of aerobic and anaerobic digesters. Digestion can result in productions of gases such as methane gas that can be captured and used as a source of fuel. In one embodiment, the gases produced are used as a source of heat in the processes described herein. In another embodiment, the digested material is used as a nutrient source for the production of additional biomass. In still another embodiment, the solids are dried and used a source of animal feed. In yet another embodiment, the solids are dried and burned as a source of energy.

In an additional embodiment, the solids are processed to provide nutrients for production of biomass, in one example, the solids are processed to provide a source of nitrogen for biomass growth. Methods for the recovery of nitrogen from biomass are known in the art, see, for example European Patent EP 1320388. For example and without limitation, the pH of residual biomass following solvent extraction can be adjusted to a pH of greater than 9.0, greater than 10.0, greater than 11.0 or greater than 12.0. The adjustment in pH can be accomplished using any base or combination of bases, for example calcium hydroxide, calcium oxide, calcium carbonate, disodium carbonate (soda ash), sodium hydroxide or potassium hydroxide. Additionally the pH adjusted residual biomass can be heated to about 40° C., about 50° C., about 60° C., about 70° C. or about 80° C. Under these conditions ammonium present in the biomass is converted to ammonia gas which can be collected in an absorption column. In one embodiment the ammonium gas is absorbed using water or an acid solution.

Alternatively or in addition, phosphorus can be recovered from the residual biomass and used for production of additional biomass. Phosphorus removal can be achieved through chemical processes, advanced biological treatment or a combination of both. Methods for removal of phosphorus are known in the art, see, for example, Yeoman et al., *Environ. Pollut.* 49:183-233 (1988). Chemical removal of phosphorus typically involves the addition of calcium, iron and aluminum salts to achieve phosphorus precipitation. Biological phosphorus removal involves the uptake of phosphorus by microorganisms in excess of their normal requirements.

The aqueous phase or raffinate can be treated to remove valuable products. For example, glycerol can be extracted from the raffinate and sold commercially. In addition, the water in the aqueous phase can, after proper treatment, be recycled to grow additional biomass. The water is expected to have useful amounts of macro and micro nutrients and minerals which will be useful in additional biomass production.

The following examples are intended to provide illustrations of the application of the present invention. The following examples are not intended to completely define or otherwise limit the scope of the invention.

EXAMPLES

Example 1

*Nannochloropsis* algae were harvested by centrifugation. The moisture content of the algal paste was 79.0 wt %, with an ash free dry weight of 17% and an ash content of 4%. The pH of the algal paste was 6.1.

For hydrothermal treatment, 400 g of algal paste was placed in a 600 ml Parr reactor (Parr Instrument Co, Moline, Ill.). The reactor was ramped from room temperature to 260° C. over 30 minutes. The reactor was held at 260° C. for 30 minutes and then cooled to room temperature over a 30 minute period. The amount of gas produced during the hydrothermal treatment was determined from the headspace volume, temperature and pressure using the ideal gas law. Analysis of the gas produced revealed that it was 97% $CO_2$. The pH of the algal paste following hydrothermal treatment was 8.5.

Following hydrothermal treatment, the pH of the material was adjusted to either pH 3, 4, 5, or 6 using 16.4 wt % sulfuric acid. The acidified material was heated to 60° C. and held at that temperature of 30 minutes with constant mixing.

Following acidification, an amount of solvent (heptane) equal to the amount of water present was added to form a solvent extraction composition which was heated to 70° C. The solvent extraction composition was then held at 70° C. for 30 minutes with constant mixing. After 30 minutes, the mixing was stopped and the composition allowed to phase separate at room temperature. The organic phase (miscella) containing the solvent and oil was decanted. The solvent was removed from the organic phase by evaporation under vacuum to obtain the oil.

The aqueous phase was extracted a second time using fresh solvent equal in volume to the amount of miscella removed. The conditions for this second extraction were the same as for the first extraction, if necessary, the pH was adjusted to 4.0 before the second extraction. The oil recovered from the two extractions was weighed to determine oil yield. The aqueous phase was filtered to recover insoluble solids which were dried and weighed. The effect of pH on yield as percent of the ash free dry weight is shown in Table 1.1

TABLE 1.1

| pH | Oil (wt %) | Solids (wt %) | Gas (wt %) |
|---|---|---|---|
| 3 | 21.3 | 9.6 | 8.0 |
| 4 | 21.3 | 16.9 | 8.0 |
| 5 | 22.2 | 22.4 | 5.8 |
| 6 | 22.0 | 23.0 | 8.1 |

Oil obtained was analyzed by Elemental Analysis and ICP-MS. Briefly, carbon, hydrogen, and nitrogen wt % were determined using an Elemental Analyzer (Perkin Elmer 240). This instrument burns samples in pure oxygen at 950° C. under static conditions to produce combustion products of $CO_2$, $H_2O$, and $N_2$ which are used to determine the wt % amounts of C, H, and N. A Thermo Finnigan FlashEA Elemental Analyzer was used for the analysis of oxygen. The instrument pyrolyzes (1060° C.) the sample in an inert atmosphere (helium) to produce carbon monoxide which is used to determine the wt % oxygen.

An Inductively Coupled Plasma Atomic Emission Spectrometer (ICP-AES) was used for multi-elemental analysis. Samples were nebulized and the resulting aerosol was transferred to the plasma torch. Optical spectrometry was used to measure emission spectra characteristic to each element. Calibration standards were used to construct calibration curves that relate the measured signal to the amount of each element present in the sample. Prior to analysis, samples were acidified and digested using appropriate sample preparation techniques. The results of the elemental analysis are shown in Table 1.2.

TABLE 1.2

| Element | Units | Extraction pH | | | |
|---|---|---|---|---|---|
| | | 3 | 4 | 5 | 6 |
| Carbon | wt % | 77.56 | 77.55 | 77.71 | 76.63 |
| Hydrogen | wt % | 10.71 | 10.97 | 10.86 | 10.82 |
| Nitrogen | wt % | 2.88 | 3.03 | 3.25 | 3.22 |
| Oxygen | wt % | 8.43 | 8.40 | 8.21 | 8.51 |
| Sulfur (ICP) | Ppm | 5247 | 5247 | 5243 | 5578 |
| Boron | Ppm | <9.77 | <8.94 | <8.30 | <8.64 |
| Calcium | Ppm | <15.3 | <12.9 | <13.2 | 2010 |
| Chromium | Ppm | <9.07 | <7.65 | <7.86 | <15.3 |
| Copper | Ppm | <9.07 | <7.65 | <7.86 | <15.3 |
| Iron | Ppm | 240 | 227 | 233 | 206 |
| Lead | Ppm | <9.77 | <8.94 | <8.3 | <8.64 |
| Lithium | Ppm | <9.77 | <8.94 | <8.3 | <8.64 |
| Magnesium | Ppm | <9.07 | <7.65 | <7.86 | 133 |
| Manganese | Ppm | <9.07 | <7.65 | <7.86 | <15.3 |
| Nickel | Ppm | <9.07 | <7.65 | <7.86 | <15.3 |
| Phosphorus | Ppm | <9.77 | <7.0 | <8.3 | 973 |
| Potassium | Ppm | <22.7 | <19.2 | <19.7 | <38.2 |
| Silicon | Ppm | 149 | 105 | 217 | 103 |
| Sodium | Ppm | <37.9 | <32.0 | <32.9 | 74.7 |
| Strotium | Ppm | <9.07 | <7.65 | <7.86 | 20.9 |
| Zinc | Ppm | 33.0 | 28.9 | 28.9 | 27.3 |

Example 2

*Nannochloropsis* algae were harvested by centrifugation. The moisture content of the algal paste was 85 wt %. The pH of the algal paste was 6.0. For hydrothermal treatment, 400 g of algal paste as placed in a 600 ml Parr reactor. The reactor was ramped from room temperature to 260° C. in 30 minutes. The reactor was then held at 260° C. for 30 minutes and then cooled to room temperature over a 30 minute period. The pH of the algal paste following hydrothermal treatment was 8.0.

For experiment 1, no acid was added after hydrothermal treatment and prior to solvent extraction. In experiment 2, the hydrothermal treated material was acidified to pH 4 prior to solvent extraction using 16.5 wt % sulfuric acid as described in Example 1. For solvent extraction, an amount of solvent (heptane equal to the amount of water present was added to form a solvent extraction composition which was heated to 70° C. The solvent extraction composition then held at 70° C. for 30 minutes with constant mixing. After 30 minutes the fluxing was stopped and the composition allowed to phase separate at room temperature. The organic phase (miscella) containing the solvent and oil was decanted. The solvent was removed from the organic phase by evaporation under vacuum to obtain the oil.

The aqueous phase was extracted a second time using fresh solvent equal in volume to the amount of miscella removed. The conditions for this second extraction were the same as for the first extraction. If necessary, the pH was adjusted to 4.0 before the second extraction in experiment 2. The oil recovered from the two extractions was weighed to determine oil yield. The aqueous phase was filtered to recover insoluble solids which were dried and weighed.

The effect of acidification following hydrothermal treatment on oil composition is shown in Table 2.1

TABLE 2.1

| Characteristic Measured | Units | Acidification Prior to Solvent Extraction | |
|---|---|---|---|
| | | No | Yes |
| Oil yield | wt % | 26.4 | 27.6 |
| Carbon | wt % | 75.3 | 77.7 |
| Hydrogen | wt % | 10.5 | 10.8 |
| Nitrogen | wt % | 3.53 | 2.52 |
| Oxygen | wt % | 7.37 | 8.44 |
| Sulfur (ICP) | Ppm | 5780 | 5250 |
| Boron | Ppm | 3.9 | 1.8 |
| Calcium | Ppm | 8500 | 1.6 |
| Chromium | Ppm | 2.7 | 0.26 |
| Copper | Ppm | 14 | 6.1 |
| Iron | Ppm | 580 | 170 |
| Lead | Ppm | 0.57 | 0.12 |
| Lithium | Ppm | 0.35 | 0.034 |
| Magnesium | Ppm | 2500 | 1.3 |
| Manganese | Ppm | 51 | 0.039 |
| Nickel | Ppm | 5.1 | 4.2 |
| Phosphorus | Ppm | 6000 | 7.2 |
| Potassium | Ppm | 270 | 11 |
| Silicon | Ppm | 39 | 7.7 |
| Sodium | Ppm | 970 | 0.64 |
| Strontium | Ppm | 110 | 0.0076 |
| Zinc | Ppm | 33 | 18 |

Example 3

*Nannochloropsis* algae were harvested by centrifugation. The moisture content of the algal paste was 86.0 wt %, with an ash free dry weight of 11% and an ash content of 3%. The pH of the algal paste was 5.3.

For hydrothermal treatment, 400 g of algal paste as placed in a 600 ml Parr reactor. The reactor was ramped from room temperature to 260° C. in 30 minutes. The reactor was then held at 260° C. for 30 minutes and then cooled to room temperature over a 30 minute period. The amount of gas produced during the hydrothermal treatment was determined from the headspace volume, temperature and pressure using the ideal gas law. The pH of the algal paste following hydrothermal treatment was 8.0.

Following hydrothermal treatment, the pH of the material was adjusted to 4 using 16.4 wt % sulfuric acid. The acidified material was heated to 60° C. and held at that temperature for 30 minutes with constant mixing.

Following acidification, an amount of solvent equal to the amount of water present was added to form a solvent extraction composition. In experiment 1, the non-polar solvent heptane was used. In experiment 2, the polar solvent MIBK (methyl isobutyl ketone) was used. MIBK is a polar solvent which is miscible in oil but not in water. The solvent extraction composition was heated to 70° C. The solvent extraction composition was then held at 70° C. for 30 minutes with constant mixing. After 30 minutes the mixing was stopped and the composition allowed to phase separate at room temperature. The organic phase (miscella) containing the solvent and oil was decanted. The solvent was removed from the organic phase by evaporation under vacuum to obtain the oil.

The aqueous phase was extracted a second time using fresh solvent equal in volume to the amount of miscella removed. The conditions for this second extraction were the same as for the first extraction. If necessary, the pH was adjusted to 4.0 before the second extraction. The oil recovered from the two extractions was weighed to determine oil yield. The aqueous phase was filtered to recover insoluble solids which were dried and weighed. The effect of solvent on yield is shown in Table 3.1

TABLE 3.1

| Solvent | Oil (wt %) | Solids (wt %) | Gas (wt %) |
|---|---|---|---|
| Heptane | 27.6 | 4.7 | 11.7 |
| MIBK | 54.7 | 11.9 | 12.3 |

Example 4

For experiments 1 through 3, *Nannochloropsis* algae were harvested by centrifugation. The moisture content of the algal paste was 78.9 wt % and the pH was 6.2.

in experiment 1, 180 g of algal paste was placed in a 600 ml Parr reactor for hydrothermal treatment. The reactor was ramped from room temperature to 300° C. in 30 minutes with mixing. The reactor was then held at 300° C. for 15 minutes and then cooled to room temperature over a 30 minute period. The pH of the algal paste after hydrothermal treatment was 8.6. Twenty five ml of 16.4 wt % sulfuric acid was added to adjust the pH to 4.0. The acid addition was done over a 30 minute period of time with mixing at 60° C. Following addition of the acid, 208 ml of Heptane was added and the temperature of the solution was ramped to 120° C. over a period of about 15 minutes with mixing. The solution was held at 120° C. with mixing for 30 minutes and then cooled to room temperature. The solution was allowed to phase separate at room temperature for 30 minutes. The organic phase (miscella) containing the solvent and oil was decanted. The solvent was removed from the organic phase by evaporation under vacuum to obtain the oil. The aqueous phase was extracted a second time using fresh solvent equal in volume to the amount of miscella removed. The conditions for this second extraction were the same as for the first extraction. Three ml of 16.4% sulfuric acid was added to readjust the pH to 4.0 prior to the second extraction. The oil recovered from the two extractions was weighed to determine oil yield. The aqueous phase was filtered to recover insoluble solids which were dried and weighed.

In experiment 2, 180 g of algal paste was placed in a 600 ml Parr reactor for hydrothermal treatment. Nine ml of 16.4% sulfuric acid was added to adjust the pH to 4.0. The reactor was ramped from room temperature to 300° C. in 30 minutes with mixing. The reactor was then mixed at 300° C. for 15 minutes and then cooled to room temperature over a 30 minute period. The pH of the algal paste after hydrothermal treatment was 7.5. Twenty two ml of 16.4 wt % sulfuric acid was added to adjust the pH to 4.0 after hydrothermal treatment. The acid addition was done over a 30 minute period of time with mixing at 60° C. Following addition of the acid, 208 ml of Heptane was added and the temperature of the solution was ramped to 120° C. over a period of about 15 minutes with mixing. The solution was held at 120° C. with mixing for 30 minutes and then cooled to room temperature. The solution was allowed to phase separate at room temperature for 30 minutes. The organic phase (miscella) containing the solvent and oil was decanted. The solvent was removed from the organic phase by evaporation under vacuum to obtain the oil. The aqueous phase was extracted a second time using fresh solvent equal in volume to the amount of miscella removed. The conditions for this second extraction were the same as for the first extraction. Two ml of 16.4% sulfuric acid was added to readjust the pH to 4.0 for the second extraction. The oil recovered from the two extractions was weighed to determine oil yield. The aqueous phase was filtered to recover insoluble solids which were dried and weighed.

in experiment 3, 180 g of algal paste was placed in a 600 ml Parr reactor for hydrothermal treatment. Nine ml of 16.4% sulfuric acid was added to adjust the pH to 4.0. The reactor was ramped from room temperature to 300° C. in 30 minutes with mixing. The reactor was then held at 300° C. for 15 minutes with mixing and then cooled to room temperature over about a 30 minute period. The pH of the algal paste after hydrothermal treatment was 7.5. Following hydrothermal treatment, 208 ml of Heptane was added and the temperature of the solution was ramped to 120° C. over a period of about 15 minutes with mixing. The solution was held at 120° C. with mixing for 30 minutes and then cooled to room temperature. The solution was allowed to phase separate at room temperature for 30 minutes. The organic phase (miscella) containing the solvent and oil was decanted. The solvent was removed from the organic phase by evaporation under vacuum to obtain the oil. The aqueous phase was extracted a second time using fresh solvent equal in volume to the amount of miscella removed. The conditions for this second extraction were the same as for the first extraction. The oil recovered from the two extractions was weighed to determine oil yield. The aqueous phase was filtered to recover insoluble solids which were dried and weighed.

Elemental analysis was performed as in Example 1. The results of Experiments 1-3 are summarized in Table 4.1. It can be seen in Table 4.1 acidification following hydrothermal treatment resulted in substantially lower P, Na and K contaminants in the extracted oil,

TABLE 4.1

| Characteristic Measured | Units | Exp. #1 | Exp. #2 | Exp. #3 |
|---|---|---|---|---|
| Oil yield | % AFDW | 27.9 | 30.0 | 31.0 |
| Acid consumption | % AFDW | 15.4 | 18.1 | 4.9 |
| Carbon | Wt % | 77.8 | 77.5 | 76.6 |
| Hydrogen | Wt % | 10.9 | 11.0 | 10.3 |
| Nitrogen | Wt % | 3.6 | 3.4 | 4.0 |
| Oxygen | Wt % | 7.5 | 7.7 | 7.5 |
| Sulfur (ICP) | Wt % | 0.65 | 0.54 | 0.63 |
| Boron | Ppm | <9 | <10 | <9 |
| Calcium | Ppm | 17 | 14 | 13 |
| Chromium | Ppm | <3 | <3 | <3 |
| Copper | Ppm | 9.1 | 10 | 9.5 |
| Lead | Ppm | <6 | <6 | <5 |
| Lithium | Ppm | <3 | <3 | <3 |
| Magnesium | Ppm | <3 | <3 | 6.9 |
| Manganese | Ppm | <3 | <3 | <3 |
| Nickel | Ppm | 3.7 | 11.0 | 7.0 |
| Phosphorus | Ppm | <6 | <6 | 42 |
| Potassium | Ppm | <15 | <9 | 230 |
| Sodium | Ppm | 10 | 14 | 386 |
| Strontium | Ppm | <3 | <3 | <3 |

Example 5

In this example, 180 g of *Nannochloropsis* algal paste with a moisture content of 78.9% and an ash content of 12.2 wt % was used for each experimental condition. The algal paste was added to the 600 ml mixed reaction chamber of a Parr reactor. The reactor vessel was purged with nitrogen and sealed. The temperature was then ramped to either 260° C. or 300° C. over a period of approximately 30 minutes. The reactor vessel was then held at the desired temperature for 0 hours (no hold time), 0.25 hours, 1 hour or 4 hours. Following the hold period the vessel was cooled to room temperature over a period of approximately 15 minutes using an ice water bath. The pH of the cooled material was adjusted to pH 4 with sulfuric acid and 200 ml of heptane added. The vessel was then sealed, heated to 120° C. and held at 120° C. for 30 minutes with constant mixing. The vessel was then cooled to room temperature and the solvent extraction material transferred to a separation funnel. The material was allowed to phase separate for about 30 minutes, after which the organic phase was decanted and filtered. The heptane was removed from the organic phase by evaporation under vacuum and the resulting oil was weighed. The aqueous phase was extracted again following the same procedure after the addition of fresh heptane. The oil resulting from the two extractions was combined.

The oil was then subjected to a simulated distillation using ASTM protocol D7169-11 (ASTM International, West Conshohocken, Pa.). The results of the simulated distillation are presented in Table 5.1. The distillation yields at 1020° F. for all oils were between 68 and 74%. The most abundant fraction was in the 630-1020° F. boiling point (BP) range (VGO range). Vacuum residue (BP>1020° F.) ranged from 26.8 to 33.5%. Increasing the hydrothermal treatment temperature from 260° C. to 300° C. caused a shift to lower boiling points.

TABLE 5.1

| HTT temp (° C.) | Time (hours) | Percent Mass Faction | | | | |
|---|---|---|---|---|---|---|
| | | 260-400° F. | 400-490° F. | 490-630° F. | 630-1020° F. | >1020° F. |
| 260 | 0 | 0.5 | 1.5 | 6.5 | 62.0 | 29.5 |
| | .25 | 1.0 | 1.3 | 7.1 | 63.8 | 26.8 |
| | 1 | 1.2 | 2.2 | 7.3 | 55.8 | 33.5 |
| | 4 | 1.5 | 3.0 | 9.5 | 54.1 | 31.9 |
| 300 | 0 | 1.3 | 2.9 | 28.0 | 42.0 | 25.8 |
| | 1 | 2.4 | 4.4 | 23.5 | 40.0 | 29.7 |
| | 4 | 2.2 | 5.0 | 24.5 | 39.2 | 29.1 |

Example 6

In these experiments, extraction with either heptane or MIBK was compared using 4 different samples of *Spirulina*. Samples A and B contained *S. platensis*, sample C contained *S. maxima* and sample D contained commercially obtained *Spirulina* whose species was unknown.

For each of the samples, 200 g of algal paste was added to a 600 ml Parr reactor and the reactor purged with nitrogen gas. The moisture content of the pastes was 83.2%, 85.0%, 84.9% and 79.6% for samples A, B, C and D, respectively. For hydrothermal treating, the paste was heated to approximately 300° C. and held there for 30 minutes with mixing at 200 rpm. After the hydrothermal treatment, the reactor was cooled to approximately 40° C. and the pH of the paste after hydrothermal treatment was determined and adjusted to approximately 4 with 16.4 wt % $H_2SO_4$. The acidified material was heated to about 60° C. and held at that temperature for 30 minutes with constant mixing. Following acid treatment, the material was cooled to about 40° C., the pH measured, and the pH readjusted to 4, if necessary. 200 ml of either heptane or MIBK was added to the reaction chamber and solvent extraction carried out at approximately 120° C. for 30 minutes with mixing at 200 rpm. Following solvent extraction, the reactor was cooled to about 40° C. and the phases allowed to gravity separate. Following separation, the organic phase was decanted and the solvent removed using a rotovap. The residual aqueous phase and biomass was subjected to a second solvent extraction using fresh solvent and the same procedure. The procedure was repeated for a total of 3 solvent extractions. Total mass of oil obtained and the percent oil yield was determined on an AFDW basis. The results as shown in Table 6.1.

TABLE 6.1

| | Oil Yield (% AFDW) | |
|---|---|---|
| Sample | Heptane | MIBK |
| A | 21.1 | 40.6 |
| B | 18.2 | 32.3 |
| C | 16.6 | 34.7 |
| D | 18.8 | 38.4 |

Example 7

In this experiment, oil yield without the use of solvent extraction was determined using the same samples as were used in Example 6. For each of samples B, C and D, 300 g of algal paste was added to a 600 ml Parr reactor. For hydrothermal treatment, the paste was heated to about 300° C. and held at that temperature for 30 minutes with mixing at 200 rpm. Following hydrothermal treatment, the reactor was cooled to about 40° C., the of the material determined, and the pH adjusted to 4 with 16.4 wt $H_2SO_4$. The acidified material was then heated to about 60° C. and held at that temperature for 30 minutes with mixing. The acidified material was then allowed to phase separate and the organic layer was decanted. The mass of oil recovered and the percent oil yield on a AFDW basis was determined. The results are shown in Table 7.1.

TABLE 7.1

| Sample | Oil Yield (% AFDW) |
|---|---|
| B | 28.6 |
| C | 18.9 |
| D | 31.7 |

Example 8

*Nannochloropsis* algae were harvested by centrifugation to produce an algal paste. The moisture content of the algal paste was 82.5 wt %. The ash free dry weight (AFDW) was 14.6%. In this example, two hydrothermal treatment temperatures (300° C. or 260° C.) and two solvents (heptane or MIBK) were used. The experimental conditions are summarized in Table 8.1.

TABLE 8.1

| Experiment | HTT Temperature | Solvent |
|---|---|---|
| A | 300° C. | Heptane |
| B | 260° C. | Heptane |
| C | 300° C. | MIBK |
| D | 260° C. | MIBK |

For each of experiments A-D, 200 g of algal paste was placed in a 600 ml Parr reactor. The paste was then heated to either 260° C. or 300° C. and held at the desired temperature for 60 minutes with constant mixing. The reactor was then cooled to room temperature and the pH adjusted to 4.0 with 16.4 wt % $H_2SO_4$. The reactor containing the acidified material was heated to 60° C. and held at that temperature with constant mixing for 30 minutes. Following the acid treatment, 200 ml of solvent was added to the reactor which was heated to 120° C. and held at that temperature for 30 minutes with mixing. Following the solvent extraction, the reactor was cooled to 40° C. and the material allowed to gravity phase separate at room temperature. After phase separation, the organic layer was removed and the remaining material subjected to two additional solvent extractions using the same procedure. After removal, the organic phase was filtered and the solvent removed using a rotovap. Mass of the oil obtained and the oil yield on an AFDW basis was calculated. The results are shown in Table 8.2.

TABLE 8.2

| Experiment | Oil Yield (% AFDW) |
|---|---|
| A | 35.8 |
| B | 30.0 |
| C | 47.6 |
| D | 48.4 |

The oil obtained was analyzed using an Agilent 7890A gas chromatograph coupled with an Agilent 5975A (inert MSD) quadrupole mass spectrometer via a heated transfer line (300° C.), A 15 m×0.25 mm i.d. Zebron ZB-1HT Inferno™ (Phenomenex, Torrance, Calif.) fused-silica capillary column with 0.1 micron film thickness was used for the experiments. The GC oven was held at 40° C. for 1 min and from there was programmed to reach 380° C. at a rate of 20° C./min remained at the upper temperature for 10 min. Helium was used as a carrier gas at a rate of 1.5 ml/min (constant flow). The mass spectrometer was operated in the full-scan mode, scanning from 20 to 800 Da, at a rate of 1.91 scans/s. The mass spectrometer was tuned in the electron ionization (EI) mode using the Agilent Autotune procedure with perfluorotributylamine (Agilent Technologies, New Castle, Del.) as calibration compound. The electron kinetic energy for the EI experiments was 70 eV. The ionization source temperature was 230° C. The temperature of the quadrupole analyzer was maintained at 150° C.

Samples were introduced into the gas chromatograph via a cold, vacuum-tight, nondiscriminating injector (Cooled Injection System-CIS 4 PTV, Gerstel, Germany). The injector temperature was programmed from 10 to 400° C. at a rate of 12° C./s. The injector temperature was maintained at 400° C. for 3 min. Dilute solutions (1 microliter aliquots) of samples (~2 wt % in $CS_2$) were introduced into the injector with a 7683B Series Agilent autosampler. The split ratio was 10:1.

Peaks in the chromatograms were defined and integrated using the Agilent system software. The nature of the individual compounds in the chromatograms was determined by matching the measured mass spectra against the reference spectra in the NIST08 and Wiley 9 libraries or by interpretation from first principles. The minimum library match quality was set to 80%. The results are shown in Table 8.3.

TABLE 8.3

| Compound | Experiment | | | |
| | A | B | C | D |
|---|---|---|---|---|
| Saturated Hydrocarbons | 1.8 | 1.0 | 1.7 | 0.8 |
| Unsaturated Hydrocarbons | 7.5 | 6.2 | 5.8 | 5.3 |
| Aromatics | 0.6 | 0.1 | 1.1 | 1.2 |
| Nitrogen Aromatics | 1.8 | 0.3 | 4.7 | 3.0 |
| Nitriles | 0.0 | 0.0 | 0.0 | 0.0 |
| Amides | 15.3 | 11.4 | 6.1 | 13.4 |
| Fatty Acids/Esters | 35.9 | 35.7 | 39.9 | 35.3 |
| Oxygen Compounds | 1.0 | 1.5 | 1.7 | 0.6 |
| Sterols/Steroids | 5.5 | 7.8 | 4.6 | 7.2 |
| Unknowns | 30.7 | 36.1 | 34.5 | 33.3 |
| Total | 100 | 100 | 100 | 100 |

Example 9

Pretreatment of Algae Paste. Two hundred grams of algae paste (76.9 wt % moisture, 12.1 wt % ash of dry matter) from a *Nannochloropsis* species of known pH was added to a 600 ml Parr reactor. The paste was heated with stirring at 100 rpm and held at 200° C. for 30 minutes (in all cases timing was begun when the temperature was within 5° C. of the target temperature). The reactor was then cooled to 40° C. and the gas pressure determined after 5 minutes. The reactor contents were then filtered using polypropylene (PP) 230 micron mesh followed by Whatman #4 filter paper. The mass and pH of the raffinate obtained were recorded. The wet solids were returned to the reactor and deionized (DI) water added to a total of 200 g as a rinse. The solids and DI water were then mixed at 100 rpm for 15 minutes at room temperature. The material from the reactor was again filtered using polypropylene 230 micron mesh followed by Whatman #4 filter paper and the mass of the raffinate and solids determined.

The wet solids were returned to the reactor and DI water added to a total of 200 grams. The solids and DI water were then heated to either 260° C. (Expt. A) or 300° C. (Expt. B) for 60 minutes with constant stifling at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

No Pretreatment of Algae Paste. Two hundred grams of algae paste (76.9 wt % moisture, 12.1 wt % ash of dry matter) from a *Nannochloropsis* species of known pH was added to a 600 ml Parr reactor. The paste was heated to either 260° C. (Expt. C) or 300° C. (Expt. D) for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was deter pined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

The results are shown in Tables 9.1, 9.2, 9.3 and 9.4. In these experiments, pretreatment reduced the amount of acid used, the amount of HTT gas produced, and the nitrogen content of the resulting oil, but decreased yield.

TABLE 9.1

| Expt | Pre-treat | HTT (° C.) | Oil Yield (wt % AFDW) | Solids (wt % AFDW) | HTT gas* (wt % AFDW) | Acid Used (wt % APDW) | Wet Solids (g) |
|---|---|---|---|---|---|---|---|
| A | Yes | 260 | 13.8 | 10.7 | 1.2 | 2.3 | 29.5 |
| B | Yes | 300 | 17.2 | 10.6 | 1.3 | 2.7 | 27.5 |
| C | No | 260 | 23.1 | 9.5 | 7.6 | 10.8 | 200 |
| D | No | 300 | 24.4 | 14.3 | 6.3 | 12.6 | 200 |

*determined by difference

TABLE 9.2

| Expt. | C (wt %) | H (wt %) | N (wt %) | S (wt %) | S** (wt %) | O* (wt %) |
|---|---|---|---|---|---|---|
| A | 78.88 | 12.06 | 1.51 | 0.60 | 0.53 | 7.0 |
| B | 80.10 | 12.2 | 1.66 | 0.49 | 0.62 | 5.6 |
| C | 78.55 | 11.86 | 2.64 | 0.53 | 0.72 | 6.4 |
| D | 79.54 | 11.85 | 2.95 | 0.45 | 0.59 | 5.2 |

*by difference
**by ICP-MS

TABLE 9.3

| ICP-MS Elemental Analysis (ppm) | | | | |
|---|---|---|---|---|
| Element | Expt. A | Expt. B | Expt. C | Expt. D |
| B | <10 | <10 | <10 | <10 |
| Na | 38.8 | 36.6 | 32.3 | <5 |
| Mg | 16.3 | 15.3 | 12.9 | 11.3 |
| Al | <5 | <5 | <5 | <5 |
| Si | 26.9 | 31.4 | 31.6 | 43.7 |
| P | 30.2 | 6.0 | 5.5 | <0.1 |
| S | 5293 | 6211 | 7197 | 5931 |
| K | <15 | <15 | <15 | <15 |
| Ca | 37.0 | 17.2 | 14.1 | 14.9 |
| Cr | <7.5 | <7.5 | <7.5 | <7.5 |
| Mn | <7.5 | <7.5 | <7.5 | <7.5 |
| Fe | 812 | 1203 | 653 | 1033 |
| Ni | 23.6 | 44.9 | 37.7 | 44.9 |
| Cu | 23.5 | 32.4 | 22.2 | 28.9 |
| Zn | 51.2 | 55.0 | 36.4 | 45.0 |
| Sr | <5 | <5 | <5 | <5 |
| Sn | <5 | <5 | <5 | <5 |
| Sb | <5 | <5 | <5 | <5 |
| Pb | <5 | <5 | <5 | <5 |

TABLE 9.4

| GC-MS Chromatogram Compound Classes | | | | |
|---|---|---|---|---|
| Compound (%) | Expt. A | Expt. B | Expt. C | Expt. D |
| Aromatics | 0.2 | 0.7 | 0.0 | 0.1 |
| Amides | 1.3 | 2.1 | 9.9 | 8.4 |
| Nitrogen Compounds | 3.5 | 0.8 | 0.2 | 3.4 |
| Fatty Acids | 49.1 | 37.1 | 28.0 | 23.1 |
| Saturated Hydrocarbons | 3.0 | 4.2 | 2.8 | 5.0 |
| Unsaturated Hydrocarbons | 8.3 | 14.6 | 9.9 | 16.5 |
| Nitriles | 0.0 | 0.0 | 0.4 | 0.6 |
| Oxygen Compounds | 12.6 | 7.6 | 11.6 | 2.4 |
| Phosphorous Compounds | 0.0 | 0.0 | 0.0 | 0.0 |
| Sterols | 4.7 | 2.6 | 6.3 | 3.0 |
| Sulfur Compounds | 0.2 | 0.0 | 0.5 | 0.0 |
| Total | 82.9 | 69.6 | 69.7 | 62.5 |

Example 10

Pretreatment. Two hundred grams of algae paste (76.8 wt % moisture, 11.3 wt % ash of dry matter) from a *Nannochloropsis* species of known pH was added to a 600 ml Parr reactor. The paste was heated with stirring at 100 rpm and held at 160° C. (Expt. A), 180° C. (Expt. B), 200° C. (Expt. C) or 220° C. (Expt. D) for 30 minutes (in all cases timing was begun when the temperature was within 5° C. of the target temperature). The reactor was then cooled to 40° C. and the gas pressure determined after 5 minutes. The reactor contents were then filtered using polypropylene 230 micron mesh followed by Whatman #4 filter paper. The mass and pH of the raffinate obtained were recorded. The wet solids were returned to the reactor and rinsed by adding deionized (DI) water to a total of 200 g. The solids and DI water were then mixed at 100 rpm for 15 minutes at room temperature. The material from the reactor was again filtered using polypropylene 230 micron mesh followed by Whatman #4 filter paper and the mass of the raffinate and solids determined. Algae paste not subjected to pretreatment was used as a control.

Hydrothermal Treatment (HTT). The wet solids were returned to the reactor and DI water added to a total of 200 grains. The solids and DI water were then heated to 260° C. for 60 minutes with constant stirring at 200 rpm. The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

Extraction. The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

The results obtained are shown in Tables 10.1, 10.2, 10.3, 10.4 and 10.5. Pretreatment at 200° C. and 220° C. resulted in the lowest amounts of amids. Pretreatment at 220° C. resulted in a decreased oil yield as compared to lower pretreatment temperatures.

TABLE 10.1

| Expt. | Pretreatment Temp (° C.) | Oil Yield (wt % AFDW) | Solids (wt % AFDW) | Gas (wt % AFDW) | Acid (wt % AFDW) | Wet Solids (wt % AFDW) |
|---|---|---|---|---|---|---|
| A | 160 | 20.2 | 12.4 | 4.6 | 8.0 | 69.6 |
| B | 180 | 19.2 | 13.7 | 2.5 | 3.6 | 51.8 |
| C | 200 | 20.7 | 15.2 | 1.2 | 2.7 | 44.7 |
| D | 220 | 13.8 | 10.3 | 1.2 | 2.2 | 30.8 |
| Control | None | 27.9 | 20.1 | 11.2 | 16.0 | 200.0 |

TABLE 10.2

| Expt. | Pretreat Temp (° C.) | Initial pH | pH post Pretreat | pH post HTT | Oil State at 25° C. |
|---|---|---|---|---|---|
| A | 160 | 6.0 | 5.9 | 8.7 | Liquid |
| B | 180 | 5.8 | 5.8 | 9.1 | Liquid |
| C | 200 | 6.0 | 6.3 | 8.9 | Liquid |
| D | 220 | 5.8 | 7.6 | 9.2 | Liquid |
| Control | None | 6.0 | — | 9.4 | Solid |

TABLE 10.3

Elemental Analysis

| Expt. | Pretreat Temp (° C.) | C (wt %) | H (wt %) | N (wt %) | S (wt %) | O* (wt %) |
|---|---|---|---|---|---|---|
| A | 160 | 78.5 | 11.9 | 2.98 | 0.60 | 6.09 |
| B | 180 | 78.9 | 11.9 | 2.28 | 0.46 | 6.50 |
| C | 200 | 78.9 | 12.0 | 2.01 | .043 | 6.75 |
| D | 220 | 79.2 | 11.8 | 1.94 | 0.47 | 6.60 |
| Control | None | 78.4 | 11.8 | 3.72 | 0.60 | 5.46 |

*by difference

TABLE 10.4

ICP-MS Results

| Element | Pretreatment Temperature (° C.) | | | | |
|---|---|---|---|---|---|
| | 160 | 180 | 200 | 220 | Control |
| B | <20 | <20 | <20 | <20 | <20 |
| Na | <15 | <15 | 20.1 | <15 | <15 |
| Mg | <5 | <5 | <5 | <5 | <5 |
| Al | <10 | <10 | <10 | <10 | <10 |
| Si | 47.5 | 42.7 | 39.3 | 58.5 | 45.5 |
| P | <5 | <5 | <5 | <5 | <5 |
| S | 3856 | 3174 | 3136 | 2088 | 2996 |
| K | <20 | <20 | <20 | <20 | <20 |
| Ca | <10 | <10 | <10 | <10 | <10 |
| Cr | <5 | <5 | <5 | <5 | <5 |
| Mn | <15 | <15 | <15 | <15 | <15 |
| Fe | 651 | 502 | 580 | 492 | 469 |
| Ni | 20.0 | 17.6 | 19.8 | 23.3 | 25.8 |
| Cu | 14.9 | 14.0 | 13.8 | 14.3 | 12.6 |
| Zn | 31.2 | 24.7 | 24.4 | 22.0 | 19.2 |
| Sr | <10 | <10 | <10 | <10 | <10 |
| Sn | <5 | <5 | <5 | <5 | <5 |
| Sb | <5 | <5 | <5 | <5 | <5 |
| Pb | <10 | <10 | <10 | <10 | <10 |

TABLE 10.5

CG-MS Compound Classes

| Compound (%) | Expt. A 160° C. | Expt. B 180° C. | Expt. C 200° C. | Expt. D 220° C. | Control No Pretreat. |
|---|---|---|---|---|---|
| Aromatics | 0.1 | 0.5 | 0.5 | 0.2 | 0.1 |
| Amides | 12.7 | 7.5 | 4.9 | 7.8 | 17.2 |
| Nitrogen compounds | 0.7 | 4.6 | 0.1 | 3.8 | 3.8 |
| Fatty Acids | 30.7 | 39.6 | 53.0 | 51.6 | 24.1 |
| Saturated Hydrocarbons | 1.6 | 1.6 | 1.3 | 1.8 | 1.3 |
| Unsaturated Hydrocarbons | 5.3 | 7.1 | 6.0 | 6.7 | 8.4 |
| Nitriles | 0.0 | 0.0 | 0.0 | 0.0 | 0.0 |
| Oxygen Compounds | 2.1 | 13.9 | 14.0 | 12.1 | 5.8 |
| Sterols | 6.1 | 5.3 | 5.6 | 4.7 | 6.4 |
| Sulfur Compounds | 0.2 | 0.0 | 0.2 | 0.4 | 0.2 |
| Unknowns | 40.5 | 20.0 | 14.3 | 11.0 | 32.8 |
| Total | 100.0 | 100.0 | 100.0 | 100.0 | 100.0 |

Example 11

Experiment A. Two hundred grams of algae paste (79.6 wt % moisture, 12.9 wt % ash of dry matter) from a *Nannochloropsis* species of known pH was added to a 600 ml Parr reactor. The paste was heated with stirring at 100 rpm and held at 180° C. for 30 minutes as a pretreatment (in all cases timing was begun when the temperature was within 5° C. of the target temperature). The reactor was then cooled to 40° C. and the gas pressure determined after 5 minutes. The reactor contents were then filtered and the mass and pH of the raffinate obtained were recorded.

The wet solids were returned to the reactor and deionized (DI) water added to a total of 200 grams. The solids and DI water were then heated to 260° C. for 60 minutes with constant stirring at 200 rpm (HTT). The reactor was then cooled to 40° C. and the pressure measured after minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

Experiment B. Two hundred grams of algae paste (79.6 wt % moisture, 12.9 wt % ash of dry matter) from a *Nannochloropsis* species of known pH was added to a 600 ml Parr reactor. The algae paste was then heated to 260° C. for 60 minutes with constant stirring at 200 rpm (MT). The reactor was then cooled to 40° C. and the pressure measured after 5 minutes. The pH of the material in the reactor was then adjusted to pH 4.0 with 164 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

Experiment C. Two hundred grams of algae paste (79.6 wt % moisture, 12.9 wt % ash of dry matter) from a *Nannochloropsis* species of known pH was added to a 600 ml Parr reactor. The paste was heated with stirring at 100 rpm and held at 180° C. for 30 minutes as a pretreatment (in all cases timing was begun when the temperature was within 0.5° C. of the target temperature). The reactor was then cooled to 40° C. and the gas pressure determined after 5 minutes. The reactor contents were then filtered and the mass of the solids and raffinate obtained was recorded.

The wet solids were returned to the reactor and DI water added to a total of 200 grams. The solids and DI water were then heated to 260° C. for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of MIBK with stirring at 200 rpm. Following extraction, the material was cooled to 40° C. and allowed to phase separate. Following separation, the organic layer was decanted, filtered and the MIBK removed using a rotovap. The mass of the oil obtained and the oil yield on an ash free dry weight basis were determined. The extraction process was repeated for a total of three extractions, after which the solids were dried and the weight recorded.

Experiment D. Four hundred grams of algae paste (79.6 wt % moisture, 17.8 wt % ash of dry matter) from a *Nannochloropsis* species of known pH was added to a 600 ml Parr reactor. The paste was heated with stirring at 100 rpm and held at 180° C. for 30 minutes as a pretreatment (in all cases timing was begun when the temperature was within 5° C. of the target temperature). The reactor was then cooled to 40° C. and the gas pressure determined after 5 minutes. The reactor contents were then filtered and the mass of the solids and raffinate obtained was recorded.

The solids were returned to the reactor and the contents heated to 260° C. for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

Experiment E. Two hundred grams of algae paste (79.6 wt % moisture, 12.9 wt % ash of dry matter) from a *Nannochloropsis* species of known pH was added to a 600 ml Parr reactor. The algae paste was then heated to 260° C. for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stifling. Following this, the pH of the material in the reactor was determined and readjusted to pH 4.0 if necessary.

The material was then solvent extracted at 120° C. for 30 minutes using 200 ml of MIBK with stirring at 200 rpm. Following extraction, the material was cooled to 40° C. and allowed to phase separate. Following separation, the organic layer was decanted, filtered and the MIBK removed using a rotovap. The mass of the oil obtained and the oil yield on an ash free dry weight basis were determined. The extraction process was repeated for a total of three extractions, after which the solids were dried and the weight recorded.

Experiment F. Four hundred grams of algae paste (79.6 wt % moisture, 17.8 wt % ash of dry matter) from a *Nannochloropsis* species of known pH was added to a 600 ml Parr reactor. The paste was heated with stirring at 100 rpm and held at 180° C. for 30 minutes as a pretreatment (in all cases timing was begun when the temperature was within 5° C. of the target temperature). The reactor was then cooled to 40° C. and the gas pressure determined after 5 minutes. The reactor contents were then filtered and the mass of the solids and raffinate obtained was recorded. The solids were returned to the reactor and an amount of deionized (DI) water equal to the amount of water removed was added. The solids and DI water were then mixed at room temperature for 15 minutes as a rinse. The rinsed material was filtered and the mass of solids and raffinate obtained was determined.

The solids were returned to the reactor and heated to 260° C. for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

Experiment G. Four hundred grams of algae paste (79.6 wt % moisture, 12.9 wt % ash of dry matter) from a *Nannochloropsis* species of known pH was added to a 600 ml Parr reactor. The paste was heated with stirring at 100 rpm and held at 180° C. for 30 minutes as a pretreatment (in all cases timing was begun when the temperature was within 5° C. of the target temperature). The reactor was then cooled to 40° C. and the gas pressure determined after 5 minutes. The reactor contents were then filtered and the mass of the solids and raffinate obtained was recorded. The solids were returned to the reactor and an amount of deionized (DI) water equal to the amount of water removed was added. The solids and DI water were then mixed at room temperature for 15 minutes as a rinse. The rinsed material was filtered and the mass of solids and raffinate obtained was determined.

The solids along with an amount of DI water equal to the amount of water removed, were returned to the reactor and heated to 260° C. for 60 minutes with constant stirring at 200 rpm (HTT). The reactor was then cooled to 40° C. and the pressure measured after 5 minutes. The of the material in the reactor was then adjusted to pH 4.0 with 16.4 wt % sulfuric acid and the acidified material held at 60° C. for 30 minutes with constant stirring. Following this, the pH of the material in the reactor was determined and readjusted to pH 4.0 if necessary.

The material was then solvent extracted at 120° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded.

The results of Experiments A-G are presented in Tables 11.1-11.5. Pretreatment reduced N, P, Si and S in the final oil. Pretreatment also reduced gas production and acid consumption.

TABLE 11.1

| Expt. | Pretreat-ment | Oil Yield (wt % AFDW) | Solids (wt % AFDW) | HTT gas* (wt % AFDW) | Acid** (wt % AFDW) | Wet Solids (g) |
|---|---|---|---|---|---|---|
| A | Yes | 25.0 | 13.4 | 2.8 | 6.2 | 53.9 |
| B | No | 30.7 | 16.6 | 11.5 | 15.4 | 200 |
| C | Yes | 36.3 | 9.7 | 3.9 | 6.2 | 49.9 |
| D | Yes | 26.7 | 18.8 | 2.2 | 4.4 | 96.7 |
| E | No | 46.7 | 12.3 | 11.5 | 14.9 | 200 |
| F | Yes | 25.9 | 11.7 | 1.4 | 3.9 | 77.7 |
| G | Yes | 19.7 | 18.6 | 1.5 | 3.3 | 41.4 |

*Gas during HTT
**% in initial AFDW

TABLE 11.2

Extracted Oil ICP-MS results

| Element | Experiment | | | | | |
|---|---|---|---|---|---|---|
| | A | B | C | D | E | F |
| B | 17.8 | 17.6 | 18.6 | 17.4 | 15.8 | 12.5 |
| Al | <10 | <10 | <10 | <10 | <10 | <10 |
| Si | 68.0 | 112 | 56.2 | 32.8 | 204 | 36.3 |
| P | <5 | 28.8 | 54.4 | <5 | 44.1 | <5 |
| S | 2893 | 4639 | 4056 | 3062 | 4559 | 2339 |
| Cr-52 | <1 | <1 | 1.38 | 1.03 | 2.00 | 1.07 |
| Cr-53 | 7.09 | 6.99 | 8.00 | 7.69 | 8.15 | 7.49 |
| Mn | <1 | <1 | <1 | <1 | <1 | <1 |
| Fe | 599 | 627 | 2412 | 1112 | 2227 | 1091 |
| Ni | 16.2 | 13.3 | 43.9 | 34.7 | 74.9 | 31.5 |
| Cu-63 | 14.2 | 15.4 | 38.0 | 19.1 | 35.0 | 19.6 |
| Cu-65 | <10 | <10 | <10 | <10 | <10 | <10 |
| Zn | 56.7 | 52.3 | 219 | 76.6 | 156 | 81.8 |
| Sr | <10 | <10 | <10 | <10 | <10 | <10 |
| Sn | <1 | <1 | <1 | <1 | <1 | <1 |
| Sb | <1 | <1 | <1 | <1 | <1 | <1 |
| Pb | <1 | <1 | <1 | <1 | <1 | <1 |

TABLE 11.3

Extracted Oil ICP-MS results

| Element | Experiment | | | | | | |
|---|---|---|---|---|---|---|---|
| | A | B | C | D | E | F | G |
| B | 31.5 | 30.8 | 32.4 | 30.9 | <20 | <20 | <10 |
| Na | 20.0 | 64.2 | 121.0 | <15 | 30.5 | 27.4 | 42.4 |
| Mg | >5 | 14.2 | 31.4 | <5 | 35.0 | <5 | 12.5 |
| Al | <10 | <10 | <10 | <10 | 189.6 | <10 | <5 |
| Si | 76, 68 | 130, 122 | 59, 56 | 41, 33 | 198, 204 | 45, 36 | 44 |
| P | <5 | 22, 29 | 46, 54 | <5 | 39, 44 | <5 | <0.1 |
| S | 3530, 2890 | 4910, 4640 | 4010, 4060 | 2940, 3060 | 4650, 4560 | 1810, 2340 | 6290 |
| K | <20 | 41.9 | 88.1 | <20 | 68.2 | <20 | <15 |
| Ca | <10 | 15.3 | 28.2 | <10 | 24.4 | <10 | 14.0 |
| Cr | <5 | <5 | <5 | <5 | <5 | <5 | <7.5 |
| Mn | <15 | <15 | <15 | <15 | <15 | <15 | <7.5 |
| Fe | 621, 599 | 649, 627 | 2445, 2412 | 1114, 1112 | 2228, 2227 | 1047, 1091 | 446 |
| Ni | 17.0 | 14.3 | 44.0 | 34.4 | 71.9 | 30.8 | 17.3 |
| Cu | 14.8 | 15.9 | 37.6 | 19.2 | 34.1 | 19.2 | 17.9 |
| Zn | 55.3 | 51.3 | 201.2 | 71.5 | 142.1 | 72.7 | 45.5 |
| Sr | <10 | <10 | <10 | <10 | <10 | <10 | <5 |
| Sn | <5 | <5 | <5 | <5 | <5 | <5 | <5 |
| Sb | <5 | <3 | <5 | <5 | <5 | <5 | <5 |
| Pb | <10 | <10 | <10 | <10 | <10 | <10 | <5 |

TABLE 11.4

Elemental analysis of extracted oil

| Expt. | Element (wt %) | | | | | |
|---|---|---|---|---|---|---|
| | C | H | N | S | S** | O* |
| A | 77.95 | 12.17 | 1.83 | 0.74 | 0.29 | 7.31 |
| B | 76.98 | 11.97 | 2.97 | 0.69 | 0.46 | 7.39 |
| C | 75.73 | 11.11 | 3.20 | 0.73 | 0.41 | 9.24 |
| D | 77.53 | 11.93 | 3.01 | 0.72 | 0.31 | 6.81 |
| E | 74.30 | 10.87 | 5.04 | 0.80 | 0.46 | 8.99 |
| F | 77.78 | 11.84 | 2.7 | 0.43 | 0.23 | 7.25 |
| G | 78.56 | 12.10 | 1.49 | 0.49 | 0.63 | 7.38 |

*by difference
**by ICP

TABLE 11.5

Compound classes by GC-MS

| Compound | Experiment | | | | | |
|---|---|---|---|---|---|---|
| | A | B | C | D | E | F |
| Aromatics | 0.1 | 0.0 | 0.0 | 0.2 | 1.4 | 0.1 |
| Amides | 9.4 | 28.3 | 10.7 | 22.1 | 19.0 | 19.0 |
| Nitrogen compounds | 5.9 | 0.7 | 0.4 | 1.6 | 2.7 | 2.1 |
| Fatty Acids | 40.6 | 23.7 | 38.1 | 26.2 | 22.2 | 31.9 |
| Saturated hydrocarbons | 2.7 | 3.5 | 0.7 | 3.3 | 1.7 | 3.2 |
| Unsaturated hydrocarbons | 6.8 | 8.2 | 6.2 | 8.2 | 6.2 | 9.6 |
| Nitriles | 0.0 | 0.0 | 0.0 | 0.1 | 0.0 | 0.3 |
| Oxygen compounds | 9.4 | 5.4 | 501 | 6.6 | 2.1 | 7.0 |
| Sterols | 6.2 | 6.9 | 4.8 | 5.2 | 6.9 | 5.6 |
| Sulfur compounds | 0.0 | 0.0 | 0.0 | 0.0 | 0.0 | 0.0 |
| Total | 81.1 | 76.7 | 65.9 | 73.5 | 62.2 | 78.7 |

Example 12

To a 2 gallon Parr reactor was added 5.5 kg of algae paste from a *Nannochloropsis* species (Moisture 83.1%, Ash of dry weight 31.8%). The pH of the paste was measured prior to addition. The paste was heated with stirring at 50 rpm and held at 200° C. for 30 minutes as a pretreatment (in all eases timing was begun when the temperature was within 5° C. of the target temperature). The reactor was then cooled to 40° C. and the aqueous phase removed. The volume and pH of the aqueous phase was measured. An amount of deionized (DI) water equal to the volume of the aqueous phase removed was added to the solids in the reactor. The solids and DI, water were mixed at 50 rpm for 15 minutes as room temperature as a rinse. The aqueous phase was removed with a pump and the volume and pH measured. Additional liquid was removed by either filtration or centrifugation.

Two hundred grams of the algae paste from the above pretreatment were added to a 600 ml Parr reactor. The pH of the paste was measured. The algae paste was then heated to 260° C. for 60 minutes with constant stirring at 200 rpm (HTT). The reactor was then cooled to 40° C. and the pressure measured after 5 minutes. The pH of the material in the reactor was then adjusted to pH 4.0 with 16.4 wt % sulfuric acid and the acidified material held at 60° C. for 30 minutes with constant stirring. Following this, the pH of the material in the reactor was determined and readjusted to 4.0 if necessary.

The material was then solvent extracted at 80° C., 100° C., 120° C. or 140° C. for 30 minutes using 200 ml of heptane with stirring at 200 rpm. Following extraction, the material was cooled to 40° C. and allowed to phase separate. Following separation, the organic layer was decanted, filtered and the heptane removed using a rotovap. The mass of the oil obtained and the oil yield on an ash free dry weight basis were determined. The extraction process was repeated for a total of three extractions, after which the solids were dried and the weight recorded. The results of the different solvent extraction temperatures are shown in Tables 12.1-12.4.

TABLE 12.1

| Extraction Temp. (° C.) | Oil Yield (wt % AFDW) | Solids (wt % AFDW) | Gas (wt % AFDW) | Acid (wt % AFDW) |
|---|---|---|---|---|
| 80 | 30.6 | 91.2 | 7.7 | 13.2 |
| 100 | 40.9 | 77.9 | 5.8 | 13.5 |
| 120 | 38.9 | 77.5 | 3.7 | 9.3 |
| 140 | 39.7 | 79.9 | 7.7 | 13.5 |

TABLE 12.2

Elemental Analysis

| Extraction Temp. (° C.) | Element (wt %) | | | | |
|---|---|---|---|---|---|
| | C | H | N | S | O* |
| 80 | 78.19 | 12.15 | 2.07 | 0.62 | 6.99 |
| 100 | 78.14 | 12.06 | 1.96 | 0.50 | 7.36 |
| 120 | 78.28 | 12.15 | 2.01 | 0.53 | 7.05 |
| 140 | 78.23 | 12.04 | 2.01 | 0.56 | 7.18 |

*by difference

TABLE 12.3

ICP-MS metals in ppm

| Element | Extraction Temperature (° C.) | | | |
|---|---|---|---|---|
| | 80 | 100 | 120 | 140 |
| B | <10 | <10 | <10 | <10 |
| Na | 38.2 | 40.6 | 37.8 | 93.3 |
| Mg | 21.9 | 13.2 | 14.3 | 15.0 |
| Al | 28.4 | 11.5 | 13.5 | <5 |
| Si | 51.7 | 30.4 | 43.1 | 26.6 |
| P | 10.7 | <0.1 | 4.2 | 27.5 |
| S | 7162 | 6476 | 5023 | 5010 |
| K | <15 | <15 | <15 | <15 |
| Ca | 33.3 | 21.6 | 22.0 | 49.7 |
| Cr | <7.5 | <7.5 | <7.5 | <7.5 |
| Mn | <7.5 | <7.5 | <7.5 | <7.5 |
| Fe | 443.0 | 462.6 | 458.3 | 525.1 |
| Ni | 17.3 | 15.1 | 14.8 | 13.2 |
| Cu | 19.7 | 19.7 | 19.1 | 20.4 |
| Zn | 45.2 | 47.8 | 42.0 | 45.8 |
| Sr | <5 | <5 | <5 | <5 |
| Sn | <5 | <5 | <5 | <5 |
| Sb | <5 | <5 | <5 | <5 |
| Pb | <5 | <5 | <5 | <5 |

TABLE 12.4

Compound Classes

| Compound (%) | Extraction Temperature (° C.) | | | |
|---|---|---|---|---|
| | 80 | 100 | 120 | 140 |
| Aromatics | 0.2 | 0.1 | 0.1 | 0.1 |
| Amides | 14.5 | 12.6 | 13.5 | 12.8 |
| Nitrogen compounds | 0.3 | 0.7 | 0.6 | 0.2 |
| Fatty acids | 45.8 | 44.8 | 46.3 | 46.8 |
| Saturated hydrocarbons | 1.2 | 0.7 | 0.8 | 0.6 |
| Unsaturated hydrocarbons | 5.2 | 5.2 | 4.2 | 4.4 |
| Nitriles | 0.0 | 0.0 | 0.0 | 0.2 |
| Oxygen compounds | 9.3 | 10.1 | 9.4 | 9.6 |
| Sterols | 3.8 | 3.6 | 3.8 | 4.0 |
| Sulfur compounds | 0.2 | 0.2 | 0.0 | 0.2 |
| Unknowns | 19.6 | 22.0 | 21.2 | 20.9 |
| Total | 100.0 | 100.0 | 100.0 | 100.0 |

Example 13

In all experiments, 200 g of algae paste and a 600 ml Parr reactor were used. The algae paste was obtained from either a *Spirulina* species (Moisture 79.5 wt %, Ash of DM % 7.2 wt %) or a *Scenedesmus* species (Moisture 85.1%, Ash of DW 13.9%).

Pretreatment. In some cases the algae paste was pretreated by heating at either 180° C. or 200° C. with stirring at 100 rpm for 10 or 30 minutes (in all cases timing was begun when the temperature was within 5 degrees of the target temperature). Pretreatment was carried out with the addition of 0 ml, 10 ml or 20 ml of 16.4 wt % sulfuric acid. The reactor was then cooled to 40° C. and gas pressure measured after 5 minutes. The material was filtered with polypropylene 230 micron mesh followed by Whatman #4 filter paper. The mass and pH of the raffinate were measured.

Rinse. In some cases the solids were rinsed after pretreatment by returning the solids to the reactor and adding deionized (DI) water to give a total of 200 g. The water and solids were then mixed at 100 rpm for 15 minutes at room temperature. The material was then filtered through polypropylene 230 micron mesh followed by Whatman #4 filter paper. The weight of the wet solids and raffinate obtained were measured.

Hydrothermal Treatment (HTT). All material was subjected to HTT. In some cases, prior to HTT, DI water was added to the wet solids to give of total of 200 g. The wet solids, with or without the added DI water, were heated at 300° C. for 60 minutes with stirring at 200 rpm. The reactor was cooled to 40° C. and then the gas pressure measured 5 minutes later.

Acidification. After HTT, the pH of the material in the reactor was adjusted to approximately 4 using 16.4 wt % sulfuric acid. The acidified material was heated and mixed for 30 minutes at 60° C. after which the pH of the material was measured and readjusted to approximately pH 4 if necessary.

Solvent Extraction. 200 ml of solvent (heptane or MIBK) was added to the reactor. Extraction was carried out at 120° C. for 30 minutes with stirring at 200 rpm. The temperature of the reactor was reduced to 40° C., the material removed, and allowed to phase separate. The organic phase was decanted, filtered and the solvent removed using a rotovap. The mass of oil and percent oil yield were determined on an AFDW basis. The material was extracted two more times for a total of three extractions.

The results obtained are presented in Tables 13.1-13.4.

TABLE 13.1

| Strain | Pretreatment Acid/Temp ° C./Time/Rinse/DI added at HTT | Solvent | Oil Yield* | Solids* | HTT gas* | Acid* After HTT | Wet Solids** |
|---|---|---|---|---|---|---|---|
| SP | 0 ml/200/30 min/yes/yes | Heptane | 8.9 | 4.8 | 2.5 | 4.8 | 11.2 |
| SP | No pretreatment | Heptane | 20.5 | 7.4 | 17.3 | 21.6 | 100 |
| SP | 0 ml/180/30 min/yes/yes | Heptane | 10.3 | 5.2 | 5.5 | 8.7 | 24.0 |
| SP | 0 ml/200/10 min/yes/yes | Heptane | 10.0 | 4.4 | 4.0 | 7.7 | 16.0 |
| SP | 10 ml/180/30 min/yes/yes | Heptane | 11.3 | 8.4 | 3.8 | 6.7 | 15.4 |
| SP | 0 ml/180/30 min/no/yes | Heptane | 13.1 | 4.5 | 6.6 | 10.6 | 20.4 |
| SP | 0 ml/180/30 min/no/yes | MIBK | 23.1 | 0.4 | 6.7 | 12.5 | 24.7 |
| SP | No pretreatment | MIBK | 36.5 | 1.2 | 17.5 | 25.0 | 100 |
| SP | 0 ml/180/130 min/no/no | Heptane | 18.6 | 18.8 | 6.1 | 8.0 | 19.9 |
| SP | 20 ml/180/30 min/no/no | Heptane | 15.7 | 13.4 | 6.2 | 8.2 | 20.8 |
| SC | 0 ml/200/30 min/yes/yes | Heptane | 10.5 | 13.3 | 2.0 | 3.6 | 13.1 |
| SC | No pretreatment | Heptane | 20.7 | 20.7 | 3.9 | 25.7 | 100 |
| SC | 0 ml/180/30 min/no/yes | Heptane | 11.3 | 20.0 | 7.9 | 8.9 | 23.0 |
| SC | 0 ml/180/30 min/no/yes | MIBK | 27.7 | 7.3 | 4.0 | 10.3 | 20.0 |
| SC | No pretreatment | MIBK | 43.3 | 10.3 | 7.9 | 36.4 | 100 |
| SC | 0 ml/180/30 min/no/yes | Heptane | 13.3 | 18.8 | 4.0 | 10.0 | 25.4 |
| SC | 0 ml/180/30 min/no/no | Heptane | 17.7 | 22.8 | 3.6 | 8.9 | 20.5 |
| SC | 20 ml/180/30 min/no/no | Heptane | 13.5 | 19.4 | 3.7 | 4.8 | 17.9 |

SP is Spirulina
SC is Scenedesmus
*wt % of AFDW
**wt %

TABLE 13.2

| Expt | Strain | Pretreatment Acid/Temp ° C./Time/Rinse/DI added at HTT | Solvent | Oil Yield (wt % AFDW) | Ph Inital | After Pretreat | After HTT |
|---|---|---|---|---|---|---|---|
| A | SP | 0 ml/200/30 min/yes/yes | Heptane | 8.9 | 6.1 | 6.3 | 9.0 |
| B | SP | No pretreatment | Heptane | 20.5 | 6.0 | — | 9.6 |
| C | SP | 0 ml/180/30 min/yes/yes | Heptane | 10.3 | 6.5 | 5.9 | 10.2 |
| D | SP | 0 ml/200/10 min/yes/yes | Heptane | 10.0 | 5.7 | 6.5 | 9.6 |

TABLE 13.2-continued

| Expt | Strain added at HTT | Pretreatment Acid/Temp ° C./Time/Rinse/DI | Solvent | Oil Yield (wt % AFDW) | Ph Initial | After Pretreat | After HTT |
|---|---|---|---|---|---|---|---|
| E | SP | 10 ml/180/30 min/yes/yes | Heptane | 11.3 | 6.4 | 5.1 | 7.8 |
| F | SP | 0 ml/180/30 min/no/yes | Heptane | 13.1 | 5.9 | 5.8 | 9.4 |
| G | SP | 0 ml/180/30 min/no/yes | MIBK | 23.1 | 5.7 | 6.1 | 10.3 |
| H | SP | No pretreatment | MIBK | 36.5 | 5.4 | — | 10.3 |
| I | SP | 0 ml/180/30 min/no/no | Heptane | 18.6 | 5.5 | 6.0 | 9.0 |
| J | SP | 20 ml/180/30 min/no/no | Heptane | 15.7 | 6.4 | 5.0 | 9.3 |
| K | SC | 0 ml/200/30 min/yes/yes | Heptane | 10.5 | 6.4 | 6.9 | 9.9 |
| L | SC | No pretreatment | Heptane | 20.7 | 6.3 | — | 8.6 |
| M | SC | 0 ml/180/30 min/no/yes | Heptane | 11.3 | 6.5 | 6.3 | 8.1 |
| N | SC | 0 ml/180/30 min/no/yes | MIBK | 27.7 | 6.0 | 6.8 | 9.9 |
| O | SC | No pretreatment | MIBK | 43.3 | 7.0 | — | 10.3 |
| P | SC | 0 ml/180/30 min/no/yes | Hepatane | 13.3 | 6.6 | 6.6 | 8.9 |
| Q | SC | 0 ml/180/30 min/no/no | Heptane | 17.7 | 7.0 | 6.6 | 9.4 |
| R | SC | 20 ml/180/30 min/no/no | Heptane | 13.5 | 7.0 | 7.6 | 8.1 |

TABLE 13.3

| Strain added at HTT | Pretreatment Acid/Temp ° C./Time/Rinse/DI | Solvent | Element (wt %) C | H | N | S | O* |
|---|---|---|---|---|---|---|---|
| SP | 0 ml/200/30 min/yes/yes | Heptane | 77.3 | 12.1 | 3.4 | 0.88 | 6.4 |
| SP | No pretreatment | Hepatic | 77.1 | 11.5 | 6.0 | 0.99 | 4.5 |
| SP | 0 ml/180/30 min/yes/yes | Heptane | 76.9 | 11.7 | 4.1 | 1.00 | 6.3 |
| SP | 0 ml/200/1.0 min/yes/yes | Heptane | 77.3 | 12.2 | 3.2 | 0.66 | 6.6 |
| SP | 10 ml/180/30 min/yes/yes | Heptane | 77.8 | 12.0 | 4.1 | 0.86 | 5.3 |
| SP | 0 ml/180/30 min/no/yes | Heptane | 76.7 | 11.3 | 4.5 | 0.67 | 6.8 |
| SP | 0 ml/180/30 min/no/yes | MIBK | 73.1 | 9.9 | 6.2 | 0.89 | 10.0 |
| SP | No pretreatment | MIBK | 73.1 | 9.8 | 7.8 | 0.82 | 8.5 |
| SP | 0 ml/180/30 min/no/no | Heptane | 77.6 | 11.4 | 6.4 | 0.54 | 4.1 |
| SP | 20 ml/180/30 min/no/no | Heptane | 77.8 | 11.5 | 5.6 | 0.78 | 4.4 |
| SC | 0 ml/200/30 min/yes/yes | Heptane | 78.6 | 11.9 | 2.3 | 0.49 | 6.8 |
| SC | No pretreatment | Heptane | 77.4 | 11.5 | 4.6 | 0.83 | 5.7 |
| SC | 0 ml/180/30 min/no/yes | Heptane | 77.8 | 11.7 | 3.0 | 0.50 | 7.1 |
| SC | 0 ml/180/30 min/no/yes | MIBK | 76.4 | 10.4 | 4.5 | 0.69 | 8.0 |
| SC | No pretreatment | MIBK | 72.9 | 10.3 | 5.8 | 0.86 | 10.1 |
| SC | 0 ml/180/30 min/no/yes | Heptane | 78.9 | 11.7 | 2.9 | 0.80 | 5.8 |
| SC | 0 ml/180/30 min/no/no | Heptane | 79.2 | 11.7 | 3.8 | 0.74 | 4.5 |
| SC | 20 ml/180/30 min/no/no | Heptane | 78.7 | 11.8 | 3.8 | 1.09 | 4.6 |

TABLE 13.4

| Compound (%) | Experiment A | B | K | L | C | D | E | F | M |
|---|---|---|---|---|---|---|---|---|---|
| Aromatics | 0.8 | 1.4 | 0.6 | 0.5 | 1.1 | 0.7 | 0.8 | 1.1 | 0.5 |
| Amides | 7.0 | 18.9 | 0.8 | 5.7 | 13.0 | 12.2 | 15.5 | 10.7 | 3.3 |
| Nitrogen compounds | 0.7 | 2.8 | 2.6 | 1/3 | 3.0 | 2.4 | 0.9 | 1.7 | 1.5 |
| Fatty Acids | 52.2 | 15.2 | 40.4 | 20.8 | 36.8 | 46.6 | 29.1 | 26.0 | 21.7 |
| Saturated hydrocarbons | 6.3 | 5.6 | 4.6 | 2.7 | 5.8 | 5.8 | 6.7 | 6.5 | 3.0 |
| Unsaturated hydrocarbons | 5.2 | 3.4 | 14.6 | 12.4 | 5.0 | 3.8 | 3.1 | 3.8 | 8.3 |
| Nitriles | 0.2 | 0.5 | 0.1 | 0.0 | 0.4 | 0.0 | 1.0 | 0.8 | 0.4 |
| Oxygen compounds | 3.5 | 2.0 | 9.9 | 8.6 | 2.7 | 2.5 | 3.4 | 14.3 | 11.6 |
| Phosphorous compounds | 0.0 | 0.0 | 0.0 | 0.0 | 0.0 | 0.0 | 0.0 | 0.0 | 0.0 |
| Sterols | 0.0 | 0.0 | 3.6 | 2.5 | 0.2 | 0.0 | 0.0 | 0.0 | 2.8 |
| Sulfur compounds | 0.4 | 0.0 | 0.0 | 0.0 | 0.5 | 0.5 | 0.8 | 0.4 | 0.0 |
| Total | 76.3 | 49.8 | 77.1 | 54.5 | 68.4 | 74.5 | 61.2 | 65.3 | 53.2 |

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments set forth herein are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the scope of the following.

What is claimed is:

1. A method for obtaining an oleaginous composition from biomass, comprising:
    (a) obtaining a feedstock comprising said biomass and water;
    (b) heating the feedstock in a closed reaction vessel to a first temperature between about 250° C. and about 360° C. and holding at said first temperature for a time between 0 minutes and about 90 minutes;
    (c) cooling the feedstock of (b) to a temperature between ambient temperature and about 150° C.;
    (d) acidifying the cooled feedstock of (c) to a pH from about 3.0 to less than 6.0 to produce an acidified composition;
    (e) heating the acidified composition of (d) to a second temperature of between about 40° C. and about 150° C. and holding the acidified composition at said second temperature for between 0 minutes and about 45 minutes;
    (f) adding to the acidified composition of (e) a volume of a solvent approximately equal in volume to the water in said acidified composition to produce a solvent extraction composition, wherein said solvent is sparingly soluble in water, but oleaginous compounds are at least substantially soluble in said solvent;
    (g) heating the solvent extraction composition in closed reaction vessel to a third temperature of between about 60° C. and about 150° C. and holding at said third temperature for a period of between about 15 minutes and about 45 minutes;
    (h) separating the solvent extraction composition into at least an organic phase and an aqueous phase;
    (i) removing the organic phase from said aqueous phase; and
    (j) removing the solvent from the organic phase to obtain an oleaginous composition.

2. The method of claim 1, wherein said biomass comprises an aquatic microorganism.

3. The method of claim 2, wherein said aquatic microorganism is a photosynthetic alga or a photosynthetic bacterium.

4. The method of claim 1, herein said first temperature is between about 260° C. and about 330° C.

5. The method of claim 1, wherein said first temperature is maintained from about 30 minutes to about 90 minutes.

6. The method of claim 1, wherein said feedstock of (c) is cooled to a temperature between about 30° C. and about 150° C.

7. The method of claim 1, wherein said cooled feedstock is acidified to a pH of between about 4.0 and about 5.0.

8. The method of claim 1, wherein said second temperature is between about 40° C. and about 100° C.

9. The method of claim 1, wherein said acidified composition is held at said second temperature from about 15 minutes to about 45 minutes.

10. The method of claim 1, wherein said third temperature is between about 110° C. and about 130° C.

11. The method of claim 1, wherein said solvent extraction composition is held at said third temperature for between about 25 minutes and about 35 minutes.

12. The method of claim 1, wherein said separating of the extraction composition into at least an organic phase and an aqueous phase is accomplished by at least one of centrifugation and gravity separation.

13. The method of claim 1, wherein said solvent is at least one of hexane, cyclohexane, heptane, toluene (methylbenzene), chloroform (trichloromethane) and methyl isobutyl ketone (MIBK).

14. The method of claim 13, wherein said solvent is methyl isobutyl ketone (MIBK).

15. The method of claim 1, further comprising repeating (I) through (h) on at least one of the aqueous phase and if present a solids phase of (i) at least once.

16. The method of claim 1, further comprising pretreating said feedstock prior to heating to said first temperature by heating said feedstock to a pretreatment temperature of between about 80° C. and about 220° C. and holding at said pretreatment temperature for between about 5 minutes and about 60 minutes to produce a pretreated feedstock.

17. The method of claim 16, further comprising removing water from said feedstock following heating.

18. The method of claim 16, further comprising storing said pretreated feedstock after said pretreatment and before heating to said first temperature.

19. The method of claim 18 wherein said pretreated feedstock is stored for a period from 1 day to 1 year.

* * * * *

UNITED STATES PATENT AND TRADEMARK OFFICE
CERTIFICATE OF CORRECTION

Page 1 of 1

PATENT NO. : 8,192,628 B2
APPLICATION NO. : 13/191373
DATED : June 5, 2012
INVENTOR(S) : Richard Cranford et al.

It is certified that error appears in the above-identified patent and that said Letters Patent is hereby corrected as shown below:

In the Claims

In Claim 15 (column 46, line 32), please change "(I)" to --(f)--.

Signed and Sealed this
Thirty-first Day of March, 2015

Michelle K. Lee
*Director of the United States Patent and Trademark Office*